US006929935B2

(12) United States Patent
Nanduri et al.

(10) Patent No.: US 6,929,935 B2
(45) Date of Patent: Aug. 16, 2005

(54) GLUCONOBACTER OXYDANS 2-KETOREDUCTASE ENZYME AND APPLICATIONS THEREOF

(75) Inventors: Venkata B. Nanduri, East Brunswick, NJ (US); Robert M. Johnston, Whitehouse Station, NJ (US); Steven L. Goldberg, Basking Ridge, NJ (US); Paul M. Cino, Bound Brook, NJ (US); Ramesh N. Patel, Bridgewater, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 61 days.

(21) Appl. No.: 10/320,104

(22) Filed: Dec. 16, 2002

(65) Prior Publication Data

US 2004/0023250 A1 Feb. 5, 2004

Related U.S. Application Data

(60) Provisional application No. 60/341,933, filed on Dec. 19, 2001.

(51) Int. Cl.[7] .................. C12N 9/02; C12N 15/00; C12N 1/20; C07H 21/04
(52) U.S. Cl. .................. 435/189; 435/4; 435/6; 435/252.3; 435/320.1; 435/69.1; 435/71.1; 435/440; 435/325; 435/254.1; 435/410; 536/23.2; 536/23.7
(58) Field of Search .................. 435/189, 4, 6, 435/252.3, 320.1, 325, 254.1, 410, 440, 69.1, 71.1; 536/23.2, 23.7, 23.1; 530/350

(56) References Cited

U.S. PATENT DOCUMENTS 5,962,290 A 10/1999 Khosla et al.

| | | | |
|---|---|---|---|
| 6,258,566 B1 | 7/2001 | Barr et al. | |
| 6,274,560 B1 | 8/2001 | Khosla et al. | |
| 6,380,370 B1 | 4/2002 | Douchette-Stamm et al. | |
| 6,605,709 B1 * | 8/2003 | Breton ...................... 536/23.1 | |

FOREIGN PATENT DOCUMENTS

| WO | WO 0078968 | 12/2000 |
|---|---|---|
| WO | WO 0134809 | 5/2001 |

OTHER PUBLICATIONS

Hage et al., "Asymmetric reduction of ketones via whole cell bioconversions and transfer hydrogenation: complementary approaches", Tetrahedron: Asymmetry, Elsevier Science Publishers, Amsterdam, NL, 12:1025–1034 (May 2001).

Database EMBL 'Online! May 2001, Kimberly WJ "Sequence 3377 from patent WO0134809", Database accession No. AX144655, XP002255433.

(Continued)

Primary Examiner—Manjunath Rao
Assistant Examiner—Yong Pak
(74) Attorney, Agent, or Firm—Audrey F. Sher

(57) ABSTRACT

This invention relates to an novel *Gluconobacter oxydans* 2-ketoreductase useful for the synthesis of chiral alcohols. Also related are isolated nucleic acids encoding *G. oxydans* 2-ketoreductase enzymes, and enzyme fragments and variants thereof, as well as vectors and host cells comprising these nucleic acids. Further related are isolated *G. oxydans* 2-ketoreductase polypeptides, and fragments and variants thereof, and antibodies that specifically bind to *G. oxydans* 2-ketoreductase polypeptides, fragments, or variants. The invention also relates to methods of obtaining isolated *G. oxydans* 2-ketoreductase nucleic acids, polypeptides, and antibodies, and methods of using *G. oxydans* 2-ketoreductase in various reactions for industrial or pharmaceutical applications.

12 Claims, 3 Drawing Sheets

OTHER PUBLICATIONS

Database EMBL Online!, Jan. 2001, Lagace et al. "Sequence 41 from patent WO078968", Database accession No. AX067466, XP002255434.

Database EMBL 'Online! Jul. 2002, Douchette–Stamm La and Bush D: "*Staphylococcus epidermidids* ORF amio acid sequence Seq. ID No.:3505", Database accession No. ABP38660, XP002255435.

Adlercreutz, P., "Asymmetric Reduction of Ketones with Enzymes from Acetic Acid Bacteria", Biotechnology Letters, vol. 13, No. 4, pp. 229–234 (1991).

Adlercreutz, P., "Novel biocatalyst for the asymmetric reduction of ketones: Permeabilized cells of *Gluconobacter oxydans*", Enzyme Microb. Technol., vol. 13, pp. 9–14 (1991).

Devaux–Basseguy, R. et al., "Potential applications of NAD(P)–dependent oxidoreductases in synthesis: A survey", Enzyme Microb. Technol., vol. 20, pp. 248–258 (1997).

Csuk, R., "Baker's Yeast Mediated Transformations in Organic Chemistry", Chem. Rev., vol. 91, pp. 49–97 (1991).

Hummel, W. et al., "Dehydrogenases for the synthesis of chiral compounds", Eur. J. Biochem., vol. 184, pp. 1–13 (1989).

Kruse, W. et al., "Alcohol–dehydrogenase–catalyzed production of chiral hydrophobic alcohols. A new approach leading to a nearly waste–free process", Recueil des Travaux Chimiques des Pays–Bas, vol. 115, pp. 239–243 (1996).

Loviny, T. et al., "Ribitol dehydrogenase of *Kiebsiella aerogenes*—Sequence of the structural gene", Biochem. J., vol. 230, pp. 579–585 (1985).

Nanduri, V.B. et al., "Purification of a stereospecific 2–ketoreductase from *Gluconobacter oxydans*", Journal of Industrial Microbiology & Biotechnology, vol. 25, pp. 171–175 (2000).

Sih, C.J. et al., "Microbial Asymmetric Catalysis—Enantioselective Reduction of Ketones", Angew. Chem. Int. Ed. Engl., vol. 23, pp. 570–578 (1984).

Sybesma, W.F.H. et al., "Reductions of 3–oxo esters by Baker's Yeast: Current Status", Biocatalysis and Biotransformation, vol. 16, pp. 95–134 (1998).

Ward, O.P. et al., "Reductive biotransforamtions of organic compounds by cells or enzymes of yeast", Enzyme Microb. Technol., vol. 12, pp. 482–493 (1990).

Zelinski, T. et al., "A Kinetic Study and Application of a Novel Carbonyl Reductase Isolated from *Rhodococcus erythropolis*", Bioorganic & Medicinal Chemistry, vol. 2, No. 6, pp. 421–428 (1994).

Zelinski, T. et al., "Purification and characterization of a novel carbonyl reductase isolated from *Rhodococcus erythropolis*", Journal of Biotechnology, vol. 33, pp. 283–292 (1994).

McPherson et al. (1988) J.Am.Chem.Soc. 120, 3267–3268.

* cited by examiner

```
-504    CGG GGN DDD SGG NSG GCG GVV ATA GGC GND GDA

-468    CCS CCT KDD TTY CCC GGR AAG AAG ACA TSS SBC YCA

-432    TGG ATG GAA ATT TCC CCA TGA TGC CCA TGG ATT TCC

-396    CSS YTG AAG ATC ATC CGG SGD AAA CGA AGG CAT CGT

-360    NAC GCC CTG GAT TTC GGG AAT ATG GAC GGA CGA CAC

-324    CAG GAC CTR AAG CCA TTC CCT CAT CGC TGA TGC CAC

-288    CAA AGG TCT CAA AAA CGG CAC TAA TGC TGT CCG TGT

-252    GGT TCA TCA AGT CCT GCC GAG GCT CTT CGT AAC GTT

-216    TAT TTA ACG CAT CCT CGC AGG CCC GGA AAC AGA TGA

-180    CCA GAG TAG GTT TAT GAA AAT TAT CCT TAC CCA GGA

-144    CAG GCC CCG TCC CCT TTG ACA CAA TCC TGT GTC AGG

-108    CCT GCC GAA CAG GCG TTT TTT TGT GGA ATA CGG AAA

-72    GCA AAG GGT TGA TGG TTC CCG CCG TCA TGG CAG TCA

-36    CAT GCC GAT GAC GGA CAA TCG AAG GAT CTT TTT TCA

M   S   L   S   G   K   I   A   A   V   T   G
   1    ATG TCC CTT TCT GGA AAA ATC GCC GCA GTC ACG GGT

A   A   Q   C   I   G   K   A   I   A   L   R
  37    GCA GCC CAG TGT ATC GGC AAG GCC ATT GCG CTT CGT
```

FIG. 1-1

```
          L   A   K   D   G   A   D   V   I   L   L   D
 73      CTG GCC AAG GAT GGC GCG GAT GTC ATC CTG CTC GAC

V   K   Q   D   T   L   A   E   T   A   K   E
109      GTC AAG CAG GAC ACG CTT GCC GAA ACC GCA AAG GAA

V   E   A   L   G   R   R   A   V   A   L   T
145      GTT GAA GCT CTC GGC CGG CGC GCT GTG GCC CTG ACG

A   D   I   S   N   R   D   Q   F   R   S   T
181      GCC GAT ATC AGC AAC CGC GAC CAG TTC CGC AGC ACG

L   A   D   A   A   K   T   L   G   G   L   D
217      CTG GCC GAT GCA GCA AAG ACG CTC GGC GGC CTG GAC

I   M   V   N   N   A   G   I   C   Q   V   K
253      ATC ATG GTC AAC AAT GCG GGG ATC TGT CAG GTC AAG

P   I   L   D   I   E   P   A   E   I   E   K
289      CCG ATC CTG GAC ATC GAG CCT GCG GAA ATC GAG AAG

I   F   S   I   N   V   Q   G   V   L   W   G
325      ATC TTC AGC ATC AAC GTT CAG GGC GTG CTC TGG GGC

M   Q   A   A   A   T   L   F   K   E   K   G
361      ATG CAG GCG GCT GCG ACC CTC TTC AAG GAG AAG GGC

T   K   G   K   I   I   N   A   C   S   I   A
397      ACC AAG GGC AAG ATC ATC AAT GCC TGC TCG ATC GCC

G   H   E   G   Y   P   L   L   G   A   Y   S
433      GGC CAT GAA GGC TAT CCC CTT CTG GGC GCC TAT TCC

A   T   K   F   A   V   R   A   L   T   Q   S
469      GCG ACC AAA TTC GCC GTC CGC GCC CTG ACG CAG TCG

A   A   K   E   L   A   S   S   G   I   T   V
505      GCC GCC AAG GAA CTC GCG TCC TCG GGC ATT ACC GTC

N   S   Y   C   P   G   I   V   G   T   D   M
541      AAT TCC TAC TGC CCC GGC ATT GTC GGA ACC GAC ATG

W   V   T   I   D   K   R   M   A   E   I   T
577      TGG GTC ACG ATC GAC AAG CGC ATG GCC GAA ATC ACC

G   T   E   I   G   A   T   Y   K   K   Y   V
613      GGT ACG GAA ATC GGC GCG ACC TAC AAG AAA TAC GTT

E   G   I   A   L   G   R   V   E   T   A   D
649      GAA GGA ATC GCT CTT GGC CGC GTG GAG ACG GCG GAC
```

FIG. 1-2

```
        D   V   A   G   F   V   A   Y   L   S   S   S
685   GAT GTG GCG GGC TTC GTC GCC TAT TTG TCC AGC AGT

D   A   D   Y   M   T   G   Q   S   V   L   I
721   GAC GCC GAT TAC ATG ACG GGT CAG TCC GTC CTG ATC

N   G   G   P   V   F   R   *------------------
757   AAC GGT GGT CCC GTT TTC CGC TGA GAT CAT AAA AAA

------------------------------------------------
769   SAG GGC CGG TTT CCC GCG CCC CCT TTT TTG TCA GCG

------------------------------------------------
781   GCC GAT CAG ACG GCC GBG CTG CCA GGC TTC GGC GGC

------------------------------------------------
793   CCC TTC CGG GTC CTG MMC TTC AAC GGA AAT GAC ATA

------------------------------------------------
805   GTC CAG GGC GCT CAT GAC CCT GTT GCC AAG CAT CAT

------------------------------------------------
817   TTC CGA AAG CTC GTC GAG NAG ATC GCT GTC CGC CTG

------------------------------------------------
829   ACG GGC CAC ATC TTC ACG CAT GAT CAT CCG GGC CGA

------------------------------------------------
841   CAT TTC TCC GCC CAG CAG GTG GGC CGG ATC CGA GCT

------------------------------------------------
853   CGG TAC CAA GCK TGA TGC ATA GCT TGA GTA
```

FIG. 1-3

GLUCONOBACTER OXYDANS 2-KETOREDUCTASE ENZYME AND APPLICATIONS THEREOF

This invention claims priority from provisional U.S. application Ser. No. 60/341,933 filed Dec. 19, 2001, which is incorporated herein by reference in its entirety.

FIELD OF THE INVENTION

This invention relates to a novel 2-ketoreductase isolated from *Gluconobacter oxydans* which catalyzes the reduction of 2-pentanone to S-(+)-2-pentanol. The invention also relates to isolated nucleic acids comprising nucleotide sequences that encode *G. oxydans* 2-ketoreductase polypeptides. Also related are vectors and host cells comprising these nucleic acids, isolated *G. oxydans* 2-ketoreductase polypeptides (e.g., recombinant polypeptides), and antibodies that specifically bind to *G. oxydans* 2-ketoreductase polypeptides. The invention further relates to methods of obtaining isolated *G. oxydans* 2-ketoreductase nucleic acids, polypeptides, and antibodies, and methods of using *G. oxydans* 2-ketoreductase in reactions required for the synthesis of industrial or pharmaceutical compounds.

BACKGROUND OF THE INVENTION

The stereospecific reduction of carbonyl groups can be used to produce chiral alcohols. Enantiomerically homogeneous chiral secondary alcohols are useful intermediates for pharmaceuticals, and may be prepared from ketones using NADH/NADPH-dependent secondary alcohol dehydrogenases. Several biochemical and chemical approaches have been employed in the synthesis of enantiomerically pure alcohols. These approaches include stereospecific chemical reduction of ketones, enzymatic hydrolysis of racemic esters, and enzymatic esterification of racemic alcohols. Notably, microbial enzymes have been used for the synthesis of chiral alcohols at laboratory, pilot, and production scale (C. J. Sih and C.-S. Chen, 1984, *Angew Chem. Int. Ed. Engl.* 23:570–578; O. P. Ward and C. S. Young, 1990, *Enzyme Microb. Technol.* 12:482–493). These synthesis reactions are typically carried out using resting cells, isolated enzymes, and/or cloned and overexpressed enzymes.

In particular, *Rhodococcus erythropolis* NADH-dependent carbonyl reductase has been used with a wide range of substrates, including 2-ketones, 3-ketones, keto-esters, and aromatic ketones (T. Zelinski and M.-R. Kula, 1994, *Bioorg. Med. Chem.* 2:421–428; T. Zelinski et al., 1994, *J. Biotechnol.* 33(3):283–92). Additionally, Baker's yeast has been widely used for the asymmetric reductive biotransformation of a variety of 2-ketones and 3-ketones (R. Csuz and B. I. Glanzer, 1991, *Chem. Rev.* 91:49–97; R. Devaux-Basseguy et al., 1997, *Enzyme Microb. Technol.* 20:248–258; W. Hummel and M.-R. Kula, 1989, *Eur. J. Biochem.* 184:1–13; W. Kruse et al., 1996, *Recl. Trav. Chim. Pays-Bas* 115:239–243; T. Loviny et al., 1985, *Biochem. J.* 230:579–85; W. F. H. Sybesma et al., 1998, *Biocatal. Biotransform.* 16:95–134; O. P. Ward and C. S. Young, 1990, *Enzyme Microb. Technol.* 12:482–493).

Similarly, *Gluconobacter oxydans* cells have been used in the reduction of various ketones to (S)-alcohols with high enantiomeric excess (P. Adlercreutz, 1991, *Enzyme Microb. Technol.* 13:9–14; P. Adlercreutz, 1991, *Biotechnol. Lett.* 13:229–234). In addition, *G. oxydans* 2-ketoreductase has been purified, and the purified polypeptide has been partly sequenced (V. Nanduri et al., 2000, *J. Indust. Microbiol. Biotechnol.* 25:171–175). However, large-scale synthesis of S-(+)-2-pentanol requires a large cell mass, i.e., a ratio of 2-pentanone to cell mass of 1 kg:50 kg. In accordance with the present invention, *G. oxydans* 2-ketoreductase was purified and cloned for overexpression in *Escherichia coli*. The disclosed 2-ketoreductase expression system thereby allows industrial production of S-(+)-2-pentanol and other chiral alcohols.

SUMMARY OF THE INVENTION

It is an object of the present invention to provide a novel 2-ketoreductase isolated from the bacterium, *Gluconobacter oxydans*, and variants, modifications, and fragments thereof.

It is also an object of the invention to provide isolated *G. oxydans* 2-ketoreductase polynucleotides, e.g., DNA and RNA molecules, comprising nucleotide sequences encoding *G. oxydans* 2-ketoreductase polypeptides, as well as nucleic acid variants, modifications, fragments, and complementary sequences thereof.

It is a further object of the present invention to provide nucleic acid probes and primers, as well as vectors and host cells, comprising *G. oxydans* 2-ketoreductase polynucleotides.

It is yet a further object of the present invention to provide isolated, recombinant *G. oxydans* 2-ketoreductase, and enzyme fragments, variants, and modifications thereof.

It is another object of the present invention to provide antibodies and antibody fragments that specifically bind to the *G. oxydans* 2-ketoreductase, or enzyme variants, modifications, or fragments thereof.

It is yet another object of the present invention to provide methods of using the *G. oxydans* 2-ketoreductase polynucleotides, vectors, and host cells to produce *G. oxydans* 2-ketoreductase.

It is still another object of the present invention to provide methods of using the recombinant *G. oxydans* 2-ketoreductase in enzymatic reactions requiring the synthesis of chiral alcohols. In various aspects, this process uses cell-free extracts or whole cells expressing recombinant *G. oxydans* 2-ketoreductase.

It is a further object of the present invention to provide methods of purifying the *G. oxydans* 2-ketoreductase, or enzyme variants, modifications, or fragments thereof, using the disclosed antibodies or antibody fragments.

Additional objects and advantages afforded by the present invention will be apparent from the detailed description and exemplification hereinbelow.

DESCRIPTION OF THE FIGURES

The appended drawings of the figures are presented to further describe the invention and to assist in its understanding through clarification of its various aspects. In the figures of the present invention, the nucleotide and amino acid sequences are represented by their one-letter abbreviations.

FIGS. 1—1 to 1–3 the nucleotide and encoded amino acid sequence of the *Gluconobacter oxydans* 2-ketoreductase gene. The bottom line shows the nucleotide sequence (SEQ ID NO:1); the top line shows the amino acid sequence (SEQ ID NO:2). In the nucleotide sequence, "Y"=C+T; "R"=A+G; "I"=deoxyinosine; "M"=A+C; "V"=A+C+G; "B"=C+T+G; "S"=C+G; "D"=A+T+G; "K"=T+G; and "N"=A+T+C+G.

DETAILED DESCRIPTION OF THE INVENTION

The present invention relates to nucleotide sequences that comprise the non-coding and protein-coding regions for a

*Gluconobacter oxydans* enzyme with ketoreductase activity. The present invention also relates to amino acid sequences encoded by these protein-coding regions. Also related are isolated nucleic acids and polypeptides comprising the disclosed sequences, as well as reagents (e.g., probes, primers, and antibodies) relating to these sequences. The *G. oxydans* nucleic acids and polypeptides of the present invention are useful for various biotechnology and pharmaceutical applications as disclosed in detail herein.

Definitions

Use of the terms "SEQ ID NO:9–SEQ ID NO:10" etc., is intended, for convenience, to refer to each individual SEQ ID NO. individually, and is not intended to refer to the sequences collectively. The invention encompasses each sequence individually, as well as any combination thereof.

"Nucleic acid or "polynucleotide" as used herein refers to purine- and pyrimidine-containing polymers of any length, either polyribonucleotides or polydeoxyribonucleotide or mixed polyribo-polydeoxyribonucleotides. This includes single-and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. Polynucleotides, e.g., oligonucleotides, include naturally-occurring species or synthetic species formed from naturally-occurring subunits or their close homologs. The term may also refer to moieties that function similarly to polynucleotides, but have non-naturally-occurring portions. Thus, polynucleotides may have altered sugar moieties or inter-sugar linkages. Exemplary among these are phosphorothioate and other sulfur containing species which are known in the art.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" or "complementary sequence" of a nucleic acid sequence as used herein refers to the antisense sequence that participates in Watson-Crick base-pairing with the original sequence.

A "probe" or "primer" refers to a nucleic acid or oligonucleotide that forms a hybrid structure with a sequence in a target region due to complementarily of at least one sequence in the probe or primer with a sequence in the target region.

"Isolated", as used herein, refers to a substantially purified *G. oxydans* molecule (e.g., nucleic acid, polypeptide, peptide, protein fusion, or antibody) that is substantially free of cellular material, culture medium, or other components. Such isolated molecules contain less than 50%, preferably less than 25%, more preferably less than 10%, and most preferably less than 1% of the components with which they were associated.

The term "vector" as used herein refers to a nucleic acid molecule capable of replicating itself and another nucleic acid molecule to which it has been linked. A vector, for example, can be a plasmid, recombinant virus, or transposon.

"Host" includes prokaryotes and eukaryotes. The term includes an organism or cell that is the recipient of a replicable vector.

A "recombinant" *G. oxydans* polypeptide or peptide refers to an amino acid sequence encoded by a *G. oxydans* nucleotide sequence described herein.

As used herein, the terms "protein" and "polypeptide" are synonymous. "Peptides" are defined as fragments or portions of polypeptides, preferably fragments or portions having at least one functional activity (e.g., catalytic or antigenic activity) as the complete polypeptide sequence.

The term "antigenic" refers to the ability of a molecule (e.g., a polypeptide or peptide) to bind to its specific antibody, or an antibody fragment, with sufficiently high affinity to form a detectable antigen-antibody complex.

A "sample" as used herein refers to a biological sample, for example, cells, cell culture media, cell components (e.g., cell membranes or cellular organelles), cell extracts (e.g., cytoplasm, cytosol, or nuclear extracts), as well as samples obtained from, for example, a laboratory procedure.

General descriptions of the foregoing terms and others are known in the art. See, e.g., Roitt et al., 1989, *Immunology*, $2^{nd}$ Edition, C. V. Mosby Company, New York; Male et al., 1991, *Advanced Immunology*, $2^{nd}$ Edition, Grower Medical Publishing, New York.

Nucleic Acids

One aspect of the present invention pertains to isolated *G. oxydans* 2-ketoreductase nucleic acids having a nucleotide sequence such as SEQ ID NO:1, or variants, modifications, fragments, or complementary sequences thereof. The nucleic acid molecules of the invention can be DNA or RNA (e.g., DNA, RNA, DNA/DNA, and DNA/RNA). A preferred nucleic acid is a DNA encoding a *G. oxydans* 2-ketoreductase (SEQ ID NO:2), or fragments or functional equivalents thereof. Such nucleic acids can comprise at least 15, 20, 21, 25, 50, 100, 200, 250, 300, 400, 500, or 1000 contiguous nucleotides.

The term "isolated" as used throughout this application refers to a *G. oxydans* 2-ketoreductase nucleic acid, polypeptide, peptide, protein fusion, or antibody, that is substantially free of cellular material, culture medium, or other components. An isolated or substantially purified molecule contains less than about 50%, preferably less than about 25%, more preferably less than about 10%, and most preferably less than 1% of the components with which it was associated.

The term "functional equivalent" is intended to include nucleotide sequences encoding functionally equivalent *G. oxydans* 2-ketoreductase. A functional equivalent of a *G. oxydans* 2-ketoreductase includes fragments or variants that perform at least one characteristic function of the enzyme (e.g., catalysis or antigenicity). For example, DNA sequence polymorphisms within the nucleotide sequence of a *G. oxydans* 2-ketoreductase polypeptide, especially those within the third base of a codon, may result in "silent" mutations, which do not affect the encoded amino acid sequence of the polypeptide due to the degeneracy of the genetic code.

Preferred embodiments include an isolated nucleic acid sharing at least 50, 54, 55, 60, 70, 77, 80, 85, 90, 95, 99, or 100% sequence identity with a polynucleotide sequence of *G. oxydans* 2-ketoreductase (e.g., SEQ ID NO:1). This polynucleotide sequence may be identical to the nucleotide sequence of *G. oxydans* 2-ketoreductase (e.g., SEQ ID NO:1), or may include up to a certain integer number of nucleotide alterations as compared to the reference sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Lesk, A. M. (Ed.), 1988, *Computational Molecular Biology*, Oxford University Press, New York; Smith, D. W. (Ed.), 1993, *Biocomputing. Informatics and Genome Projects*, Academic Press, New York; Griffin, A. M., and Griffin, H. G. (Eds.), 1994, *Computer Analysis of Sequence Data, Part I*, Humana Press, New Jersey; von Heinje, G., 1987, *Sequence Analysis in Molecular Biology*, Academic Press; Gribskov, M. and Devereux, J. (Eds.), 1991, *Sequence Analysis Primer*, M. Stockton Press, New York; and Carillo, H., and Lipman, D., 1988, *SIAM J. Applied Math.* 48:1073.

For nucleic acids, sequence identity can be determined by comparing a query sequences to sequences in publicly available sequence databases (NCBI) using the BLASTN2 algorithm (S. F. Altschul et al., 1997, *Nucl. Acids Res.*, 25:3389–3402). The parameters for a typical search are: E=0.05, v=50, B=50, wherein E is the expected probability score cutoff, V is the number of database entries returned in the reporting of the results, and B is the number of sequence alignments returned in the reporting of the results (S. F. Altschul et al., 1990, *J. Mol. Biol.*, 215:403–410).

In another approach, nucleotide sequence identity can be calculated using the following equation: % identity= (number of identical nucleotides)/(alignment length in nucleotides)*100. For this calculation, alignment length includes internal gaps but not includes terminal gaps. Alternatively, nucleotide sequence identity can be determined experimentally using the specific hybridization conditions described below.

In accordance with the present invention, nucleic acid alterations are selected from the group consisting of at least one nucleotide deletion, substitution, including transition and transversion, insertion, or modification (e.g., via RNA or DNA analogs, dephosphorylation, methylation, or labeling). Alterations may occur at the 5' or 3' terminal positions of the reference nucleotide sequence or anywhere between those terminal positions, interspersed either individually among the nucleotides in the reference sequence or in one or more contiguous groups within the reference sequence. Alterations of a nucleic acid sequence of *G. oxydans* 2-ketoreductase (e.g., SEQ ID NO:1) may create nonsense, missense, or frameshift mutations in the coding sequence, and thereby alter the polypeptide encoded by the nucleic acid.

The present invention also encompasses naturally-occurring nucleotide polymorphisms of *G. oxydans* 2-ketoreductase (e.g., SEQ ID NO:1). As will be understood by those in the art, the genomes of all organisms undergo spontaneous mutation in the course of their continuing evolution generating variant forms of gene sequences (Gusella, 1986, *Ann. Rev. Biochem.* 55:831–854). Restriction fragment length polymorphisms (RFLPs) include variations in DNA sequences that alter the length of a restriction fragment in the sequence (Botstein et al., 1980, *Am. J. Hum. Genet.* 32, 314–331). Short tandem repeats (STRs) include tandem di-, tri- and tetranucleotide repeated motifs, also termed variable number tandem repeat (VNTR) polymorphisms.

Single nucleotide polymorphisms (SNPs) are far more frequent than RFLPS, STRs, and VNTRs. SNPs may occur in protein coding (e.g., exon), or non-coding (e.g., intron, 5'UTR, and 3'UTR) sequences. SNPs in protein coding regions may comprise silent mutations that do not alter the amino acid sequence of a protein. Alternatively, SNPs in protein coding regions may produce conservative or non-conservative amino acid changes, described in detail below. In non-coding sequences, SNPs may also result in defective protein expression (e.g., as a result of defective splicing). Other single nucleotide polymorphisms have no phenotypic effects.

Further encompassed by the present invention are nucleic acid molecules that share moderate homology with the *G. oxydans* 2-ketoreductase nucleic acid sequence (e.g., SEQ ID NO:1 or a complementary sequence), and hybridize to a *G. oxydans* 2-ketoreductase nucleic acid molecule under moderate stringency hybridization conditions. More preferred are nucleic acid molecules that share substantial homology with a *G. oxydans* 2-ketoreductase nucleic acid sequence (e.g., SEQ ID NO:1 or a complementary sequence) and hybridize to *G. oxydans* 2-ketoreductase nucleic acid molecules under high stringency hybridization conditions.

As used herein, the phrase "moderate homology" refers to sequences which share at least 60% sequence identity with a ketoreductase sequence (e.g., SEQ ID NO:1), whereas the phrase "substantial homology" refers to sequences that share at least 90% sequence identity with a ketoreductase sequence. It is recognized, however, that polypeptides and the nucleic acids encoding such polypeptides containing less than the above-described level of homology arising as splice variants or that are modified by conservative amino acid substitutions (or substitution of degenerate codons) are contemplated to be within the scope of the present invention.

The phrase "hybridization conditions" is used herein to refer to conditions under which a double-stranded nucleic acid hybrid is formed from two single nucleic acid strands, and remains stable. As known to those of skill in the art, the stability of the hybrid sequence is reflected in the melting temperature ($T_m$) of the hybrid (see F. M. Ausubel et al. (Eds.), 1995, *Current Protocols in Molecular Biology*, John Wiley and Sons, Inc., New York, N.Y.). The $T_m$ decreases approximately 0.5° C. to 1.5° C. with every 1% decrease in sequence homology. In general, the stability of a hybrid sequence is a function of the length and guanine/cytosine content of the hybrid, the sodium ion concentration, and the incubation temperature. Typically, the hybridization reaction is initially performed under conditions of low stringency, followed by washes of varying, but higher, stringency. Reference to hybridization stringency relates to such washing conditions.

In accordance with the present invention, "high stringency" conditions can be provided, for example, by hybridization in 50% formamide, 5×Denhardt's solution, 5×SSPE, and 0.2% SDS at 42° C., followed by washing in 0.1×SSPE and 0.1% SDS at 65° C. By comparison, "moderate stringency" can be provided, for example, by hybridization in 50% formamide, 5×Denhardt's solution, 5×SSPE, and 0.2% SDS at 42° C., followed by washing in 0.2×SSPE and 0.2% SDS at 65° C. In addition, "low stringency" conditions can be provided, for example, by hybridization in 10% formamide, 5×Denhardt's solution, 6×SSPE, and 0.2% SDS at 42° C., followed by washing in 1×SSPE and 0.2% SDS at 50° C. It is understood that these conditions may be varied using a variety of buffers and temperatures well known to those skilled in the art.

In a preferred embodiment of the present invention, the nucleic acid is a DNA molecule encoding at least a fragment of a *G. oxydans* 2-ketoreductase (SEQ ID NO:2). A nucleic acid molecule encoding a *G. oxydans* 2-ketoreductase can be obtained from mRNA present in *Gluconobacter oxydans* cells. It may also be possible to obtain nucleic acid molecules encoding a 2-ketoreductase from *Gluconobacter oxydans* genomic DNA. In addition, a nucleic acid encoding a *G. oxydans* 2-ketoreductase can be cloned from either a cDNA or a genomic library in accordance with the protocols described in detail herein.

Nucleic acids encoding *G. oxydans* 2-ketoreductase enzymes can also be cloned using established polymerase chain reaction (PCR) techniques (see K. Mullis et al., 1986, *Cold Spring Harbor Symp. Quant. Biol.* 51:260; K. H. Roux, 1995, *PCR Methods Appl.* 4:S185) in accordance with the nucleic acid sequence information provided herein. For example, PCR techniques can be used to produce the nucleic acids of the invention, using either RNA (e.g., mRNA) or DNA (e.g., genomic DNA) as templates. Primers used for PCR can be synthesized using the sequence information provided herein and can further be designed to introduce appropriate new restriction sites, if desirable, to facilitate incorporation into a given vector for recombinant expression.

The nucleic acid molecules of the invention, or fragments thereof, can also be chemically synthesized using standard techniques. Various methods of chemically synthesizing polydeoxynucleotides are known, including solid-phase synthesis which, like peptide synthesis, has been fully automated in commercially available DNA synthesizers (see, for example, U.S. Pat. No. 4,598,049 to Itakura et al.; U.S. Pat. No. 4,458,066 to Caruthers et al.; U.S. Pat. Nos. 4,401,796 and 4,373,071 to Itakura).

It will be appreciated by one skilled in the art that variations in one or more nucleotides (up to about 3–4% of the nucleotides) of the nucleic acid molecules encoding a *G. oxydans* 2-ketoreductase may exist among organisms within a population due to natural allelic variation. Any and all such nucleotide variations and resulting amino acid polymorphisms are within the scope of the invention. Furthermore, there may be one or more isoforms or related family members of the *G. oxydans* 2-ketoreductase described herein. Such isoforms or family members are defined as polypeptides that are related in function and amino acid sequence to a *G. oxydans* 2-ketoreductase (e.g., SEQ ID NO:2), but encoded by genes at different loci. In addition, it is possible to modify the DNA sequence of the *G. oxydans* 2-ketoreductase gene using genetic techniques to produce proteins or peptides with altered amino acid sequences.

DNA sequence mutations can be introduced into a nucleic acid encoding a *G. oxydans* 2-ketoreductase by any one of a number of methods, including those for producing simple deletions or insertions, systematic deletions, insertions or substitutions of clusters of bases or substitutions of single bases, to generate desired variants. Mutations of the *G. oxydans* 2-ketoreductase nucleic acid molecule to generate amino acid substitutions or deletions are preferably obtained by site-directed mutagenesis.

Site directed mutagenesis systems are well known in the art, and can be obtained from commercial sources (see, for example, Amersham-Pharmacia Biotech, Inc., Piscataway, N.J.). Guidance in determining which amino acid residues may be substituted, inserted, or deleted without abolishing biological or immunological activity may be found using computer programs well known in the art, for example, DNASTAR software (DNASTAR, Inc., Madison, Wis.). Mutant forms of the *G. oxydans* 2-ketoreductase nucleic acid molecules are considered within the scope of the present invention, where the expressed polypeptide or peptide is capable catalytic or antigenic activity.

A fragment of the nucleic acid molecule encoding a *G. oxydans* 2-ketoreductase is defined as a nucleotide sequence having fewer nucleotides than the nucleotide sequence encoding the entire amino acid sequence of the enzyme. In one embodiment of the present invention, a nucleic acid molecule corresponding to a fragment of a *G. oxydans* 2-ketoreductase nucleic acid sequence can be used as a probe for assaying a biological sample (e.g., from cells or cell extracts), the expression of one or more enzymes, or as a primer for DNA sequencing or PCR amplification. Preferably, such fragments are at least 8, 12, 15, 20, 21, or 25 contiguous nucleotides in length.

In certain embodiments, the nucleic acid molecules of the invention may include linker sequences, modified restriction endonuclease sites, and other sequences useful for molecular cloning, expression, or purification of recombinant protein or fragments thereof. Nucleic acid molecules in accordance with the present invention may also be conjugated with radioisotopes, or chemiluminescent, fluorescent, or other labeling compounds (e.g., digoxigenin). In addition, the nucleic acid molecules of the present invention may be modified by nucleic acid modifying enzymes, for example, kinases or phosphatases. These and other modifications of nucleic acid molecules are well known in the art. In addition, a nucleic acid molecule that encodes a *G. oxydans* 2-ketoreductase, or a functional fragment thereof, can be ligated to a heterologous sequence to encode a fusion protein (also called a chimeric protein) as described in detail herein.

Vectors and Host Cells

Another aspect of the present invention pertains to vectors comprising a nucleic acid encoding a *G. oxydans* 2-ketoreductase, as described herein, operably linked to at least one regulatory sequence. "Operably linked" is intended to mean that the nucleotide acid sequence is linked to a regulatory sequence in a manner that allows expression of the nucleotide sequence (i.e., production of mRNA and/or amino acid sequences). Regulatory sequences are known in the art and are selected to direct expression of the desired protein in an appropriate host cell or cell-free expression system. Accordingly, the term regulatory sequence includes promoters, enhancers and other expression control elements (see D. V. Goeddel, 1990, *Methods Enzymol.* 185:3–7). It should be understood that the design of the expression vector may depend on such factors as the choice of the host cell or expression system to be utilized and/or the type of polypeptide desired to be expressed.

Suitable expression vectors include, but are not limited to, pUC, pBluescript (Stratagene), pET (Novagen, Inc., Madison, Wis.), as well as pREP, pSE420, and pLEX (Invitrogen). Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Preferred replication and inheritance systems include M13, ColE1, SV40, baculovirus, lambda, adenovirus, CEN ARS, 2 µm, ARS, and the like. Several regulatory elements (e.g., promoters) have been isolated and shown to be effective in the transcription and translation of heterologous proteins in the various hosts. Such regulatory regions, methods of isolation, manner of manipulation, etc. are known in the art. Non-limiting examples of bacterial promoters include the β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters.

Non-limiting examples of yeast promoters include the 3-phosphoglycerate kinase promoter, glyceraldehyde-3- phosphate dehydrogenase (GAFDH or GAP) promoter, galactokinase (GAL1) promoter, galactoepimerase promoter, and alcohol dehydrogenase (ADH1) promoter. Suitable promoters for mammalian cells include, without limitation, viral promoters, such as those from Simian Virus 40 (SV40), Rous sarcoma virus (RSV), adenovirus (ADV), and bovine papilloma virus (BPV). Alternatively, the endogenous *G. oxydans* regulatory elements (e.g., in SEQ ID NO:1) can be used.

Eukaryotic cells may also require terminator sequences, polyadenylation sequences, and enhancer sequences that modulate gene expression. Sequences that cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or preprotein or proprotein sequences, may also be included in accordance with established methods. Secretory signal sequences are generally positioned 5' to the nucleotide sequence encoding the protein of interest, although certain signal sequences can be positioned 3' to the nucleotide sequence of interest (see, e.g., Welch et al., U.S. Pat. No. 5,037,743; Holland et al., U.S. Pat. No. 5,143,830). Cell-specific secretory signals can be used with certain cell types (e.g., yeast cells).

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that 1) confer resistance to antibiotics or other toxic substances, e.g., ampicillin, neomycin, methotrexate, etc.; 2) complement auxotrophic deficiencies, or 3) supply critical nutrients not available from complex media, e.g., the gene encoding D-alanine racemase for Bacilli. Markers may be an inducible or non-inducible gene and will generally allow for positive selection. Non-limiting examples of markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts are understood by those of skill in the art.

Suitable cell-free expression systems for use with the present invention include, without limitation, rabbit reticulocyte lysate, wheat germ extract, canine pancreatic microsomal membranes, *E. coli* S30 extract, and coupled transcription/translation systems (Promega Corp., Madison, Wis.). Suitable host cells include bacteria, fungi, yeast, plant, insect, and animal, mammalian, and human cells. Specifically included are SF9, C129, 293, NIH 3T3, CHO, COS, HeLa, and *Neurospora* cells. Insect cell systems (i.e., lepidopteran host cells and baculovirus expression vectors) (Luckow and Summers, 1988, *Biotechnology* 6:47–55) are also included.

Preferred host cells include fungal cells, such as *Aspergillus* (*A. niger, A. oryzae*, and *A. fumigatus*), *Fusarium venenatum, Schizosaccharomyces pombe, Saccharomyces cerevisiae, Kluyveromyces lactis, Kluyveromyces fragilis, Ustilago maydis, Candida* (e.g., *C. albicans, C. methylica, C. boidinii, C. tropicalis, C. wickerhamii, C. maltosa*, and *C. glabrata*), *Hansenula* (e.g., *H. anomala, H. polymorpha, H. wingei, H. jadinii* and *H. satumus*); and *Pichia* (e.g., *P. angusta, P. pastoris, P. anomala, P. stipitis, P. methanolica*, and *P. guilliermondii*) cells. Particularly preferred are bacterial cells, such as *Staphylococcus aureus, Escherichia coli, Bacillus* (e.g., *B. licheniformis, B. amyloliquefaciens*, and *B. subtilis*) and *Streptomyces* (e.g., *Streptomyces lividans* and *Streptomyces coelicolor*) cells.

In general, host cells can be transformed, transfected, or infected as appropriate by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, e.g., by injection (see, Kubo et al., 1988, *FEBS Letts.* 241:119).

Methods for transforming *S. cerevisiae* cells with exogenous DNA and producing recombinant proteins therefrom are found in, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075, and Kawasaki et al., U.S. Pat. No. 4,931,373). Transformation methods for other yeasts, including *H. polymorpha/P. angusta, S. pombe, K. lactis, K. fragilis, U. maydis, P. pastoris, P. methanolica/C. methylica*, and *C. maltosa* are known in the art (see, for example, Gleeson et al., 1986, *J. Gen. Microbiol.* 132:3459–3465; Cregg, U.S. Pat. No. 4,882,279; and Hiep et al., 1993, *Yeast* 9:1189–1197). *Aspergillus* cells can be transformed according to the methods of McKnight et al., U.S. Pat. No. 4,935,349, while *Acremonium chrysogenum* cells can be transformed in accordance with Sumino et al., U.S. Pat. No. 5,162,228. In general, host cells may integrate the nucleic acid molecules of this invention into chromosomal loci. Alternatively, the host cells may maintain the nucleic acid molecules via episomal vectors.

In one embodiment, an expression vector comprises a nucleic acid encoding at least a fragment of a *G. oxydans* 2-ketoreductase. In another embodiment, the expression vector comprises a DNA sequence encoding at least a fragment of a *G. oxydans* 2-ketoreductase fused in-frame to a DNA sequence encoding a heterologous polypeptide or peptide. Such expression vectors can be used to transfect host cells to thereby produce *G. oxydans* 2-ketoreductase polypeptides or peptides, including fusion proteins or peptides encoded by nucleic acid molecules as described below.

Several well-established techniques can be used to determine the expression levels and patterns of *G. oxydans* 2-ketoreductase. For example, mRNA levels can be determined utilizing Northern blot analysis (J. C. Alwine et al., 1977, *Proc. Natl. Acad. Sci. USA* 74:5350–5354; I. M. Bird, 1998, *Methods Mol. Biol.* 105:325–36), whereby poly(A)$^+$ RNA is isolated from cells, separated by gel electrophoresis, blotted onto a support surface (e.g., nitrocellulose or Immobilon-Ny+ (Millipore Corp., Bedford, Mass.)), and incubated with a labeled (e.g., fluorescently labeled or radiolabeled) oligonucleotide probe that is capable of hybridizing with the mRNA of interest.

Alternatively, mRNA levels can be determined by quantitative (for review, see W. M. Freeman et al., 1999, *Biotechniques* 26:112–122) or semi-quantitative RT-PCR analysis (Ren et al., *Mol. Brain Res.* 59:256–63). In accordance with this technique, poly(A)$^+$ RNA is isolated from cells, used for cDNA synthesis, and the resultant cDNA is incubated with PCR primers that are capable of hybridizing with the template and amplifying the template sequence to produce levels of the PCR product that are proportional to the cellular levels of the mRNA of interest. Another technique, in situ hybridization, can also be used to determine mRNA levels (reviewed by A. K. Raap, 1998, *Mutat. Res.* 400:287–298). In situ hybridization techniques allow the visual detection of mRNA in a cell by incubating the cell with a labeled (e.g., fluorescently labeled or digoxigenin labeled) oligonucleotide probe that hybridizes to the mRNA of interest, and then examining the cell by microscopy.

*G. oxydans* 2-ketoreductase fragments, modifications, or variants can be also assessed directly by well-established techniques. For example, host cell expression of the recombinant polypeptides can be evaluated by western blot analysis using antibodies specifically reactive with these polypeptides (see above). Production of secreted forms of the polypeptides can be evaluated by immunoprecipitation using monoclonal antibodies that are specifically reactive the polypeptides. Other, more preferred, assays take advantage of the functional characteristics of *G. oxydans* 2-ketoreductase. As previously set forth, *G. oxydans* 2-ketoreductase can be used in various reactions to generate chiral alcohols. Thus, *G. oxydans* 2-ketoreductase function can be assessed by measuring the products of these reactions. In specific aspects, any one of the assays described hereinbelow can be employed.

Polypeptides

A further aspect of the present invention pertains to *G. oxydans* 2-ketoreductase polypeptides (e.g., recombinant polypeptides). The present invention encompasses a *G. oxydans* 2-ketoreductase polypeptide (e.g., SEQ ID NO:2), and fragments and functional equivalents thereof. Such polypeptides can comprise at least 5, 12, 20, 21, 25, 30, 32, 35, 50, 100, 170, 200, 210, 300, or 500 contiguous amino acid residues. Preferred are polypeptides that share moderate homology with a *G. oxydans* 2-ketoreductase polypeptide (e.g., SEQ ID NO:2). More preferred are polypeptides that share substantial homology with a *G. oxydans* 2-ketoreductase polypeptide.

The term "functional equivalent" is intended to include proteins which differ in amino acid sequence from the *G. oxydans* 2-ketoreductase polypeptide (e.g., SEQ ID NO:2), but where such differences result in a modified protein which performs at least one characteristic function of polypeptide (e.g., catalytic or antigenic activity). For example, a functional equivalent of a *G. oxydans* 2-ketoreductase polypeptide may have a modification such as a substitution, addition or deletion of an amino acid residue which is not directly involved in the function of this polypeptide. Various modifications of the *G. oxydans* 2-ketoreductase polypeptide to produce functional equivalents of these polypeptides can be made in accordance with established methods.

It is also possible to modify the structure of a *G. oxydans* 2-ketoreductase polypeptide for such purposes as increasing solubility, enhancing reactivity, or increasing stability (e.g., shelf life ex vivo and resistance to proteolytic degradation in vivo). Such modified proteins are considered functional equivalents of a *G. oxydans* 2-ketoreductase polypeptide as defined herein. Preferably, *G. oxydans* 2-ketoreductase polypeptides are modified so that they retain catalytic activity. Those residues shown to be essential for activity can be modified by replacing the essential amino acid with another, preferably similar amino acid residue (a conservative substitution) whose presence is shown to enhance, diminish, but not eliminate, or not effect receptor interaction. In addition, those amino acid residues that are not essential for catalysis can be modified by being replaced by another amino acid whose incorporation may enhance, diminish, or not effect reactivity.

In order to enhance stability and/or reactivity, a *G. oxydans* 2-ketoreductase polypeptide can be altered to incorporate one or more polymorphisms in the amino acid sequence. Additionally, D-amino acids, non-natural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, *Int. Arch. Allergy Appl. Immunol.* 64(1):84–99) to produce a protein conjugated with PEG. In addition, PEG can be added during chemical synthesis of the protein. Other possible modifications include phosphorylation, sulfation, reduction/alkylation (Tarr, 1986, *Methods of Protein Microcharacterization*, J. E. Silver (Ed.) Humana Press, Clifton, N.J., pp. 155–194); acylation (Tarr, supra); chemical coupling (Mishell and Shiigi (Eds.), 1980, *Selected Methods in Cellular Immunology*, W H Freeman, San Francisco, Calif.; U.S. Pat. No. 4,939,239); and mild formalin treatment (Marsh, 1971, *Int Arch. of Allergy and Appl. Immunol.* 41:199–215).

Modified polypeptides can have conservative changes, wherein a substituted amino acid has similar structural or chemical properties, e.g., replacement of leucine with isoleucine. More infrequently, a modified polypeptide can have non-conservative changes, e.g., substitution of a glycine with a tryptophan. Guidance in determining which amino acid residues can be substituted, inserted, or deleted without abolishing biological or immunological activity can be found using computer programs well known in the art, for example, DNASTAR software (DNASTAR, Inc., Madison, Wis.)

As non-limiting examples, conservative substitutions in the *G. oxydans* 2-ketoreductase amino acid sequence can be made in accordance with the following table:

| Original Residue | Conservative Substitution(s) |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunogenicity can be made by selecting substitutions that are less conservative than those shown in the table, above. For example, non-conservative substitutions can be made which more significantly affect the structure of the polypeptide in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Preferred polypeptide embodiments further include an isolated polypeptide comprising an amino acid sequence sharing at least 50, 54, 55, 60, 70, 80, 85, 86, 90, 95, 97, 98, 99, 99.5 or 100% identity with the amino acid sequence of *G. oxydans* 2-ketoreductase (SEQ ID NO:2). This polypeptide sequence may be identical to the sequence of *G. oxydans* 2-ketoreductase (SEQ ID NO:2), or may include up to a certain integer number of amino acid alterations as compared to the reference sequence Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, *Bioinformatics: Sequence and Genome Analysis*, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch, 1970, *J. Mol. Biol.* 48:443–453; 2) BLOSSUM62 comparison matrix from Hentikoff and Hentikoff, 1992, *Proc. Natl. Acad. Sci. USA* 89:10915–10919; 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity=(the number of identical residues)/(alignment length in amino acid residues)*100. For this calculation, alignment length includes internal gaps but does not include terminal gaps.

In accordance with the present invention, polypeptide sequences may be identical to the sequence of *G. oxydans* 2-ketoreductase (e.g., SEQ ID NO:2), or may include up to a certain integer number of amino acid alterations. Polypeptide alterations are selected from the group consisting of at least one amino acid deletion, substitution, including conservative and non-conservative substitution, or insertion. Alterations may occur at the amino- or carboxy-terminal positions of the reference polypeptide sequence or anywhere between those terminal positions, interspersed either individually among the amino acids in the reference sequence or in one or more contiguous groups within the reference sequence. In specific embodiments, polypeptide variants may be encoded by *G. oxydans* 2-ketoreductase nucleic acids comprising single nucleotide polymorphisms and/or alternate splice variants.

*G. oxydans* 2-ketoreductase polypeptides may also be modified by conjugation with a label capable of providing a detectable signal, either directly or indirectly, including, for example, radioisotopes and fluorescent compounds. Non-limiting examples of fluorescent compounds include Cy3, Cy5, GFP (e.g., EGFP, DsRed, dEFP, etc. (CLONTECH, Palo Alto, Calif.)), Alexa, BODIPY, fluorescein (e.g., FluorX, DTAF, and FITC), rhodamine (e.g., TRITC), auramine, Texas Red, AMCA blue, and Lucifer Yellow. Suitable isotopes include, but are not limited to, $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

The invention also relates to isolated, synthesized and/or recombinant portions or fragments of a *G. oxydans* 2-ketoreductase polypeptide (e.g., SEQ ID NO:2), as described herein. Polypeptide fragments (i.e., peptides) can be made which have full or partial function on their own, or which when mixed together (though fully, partially, or nonfunctional alone), spontaneously assemble with one or more other polypeptides to reconstitute a functional protein having at least one functional characteristic of a *G. oxydans* 2-ketoreductase of this invention. In addition, *G. oxydans* 2-ketoreductase polypeptide fragments may comprise, for example, one or more domains of the polypeptide (e.g., a short chain dehydrogenase domain) disclosed herein.

The polypeptides of the present invention, including function-conservative variants, may be isolated from wild-type or mutant *G. oxydans* cells, from heterologous organisms or cells (e.g., bacteria, yeast, insect, plant, or mammalian cells) comprising recombinant *G. oxydans* 2-ketoreductase, or from cell-free translation systems (e.g., wheat germ, microsomal membrane, or bacterial extracts) in which a *G. oxydans* 2-ketoreductase protein-coding sequence has been introduced and expressed. Furthermore, the polypeptides may be part of recombinant fusion proteins. The polypeptides can also, advantageously, be made by synthetic chemistry. Polypeptides may be chemically synthesized by commercially available automated procedures, including, without limitation, exclusive solid phase synthesis, partial solid phase methods, fragment condensation or classical solution synthesis.

Isolation of Polypeptides

Yet another aspect of the present invention pertains to methods of isolating *G. oxydans* 2-ketoreductase polypeptides, or variants, modifications, or fragments thereof from biological samples (e.g., cells, cell extracts or lysates, cell membranes, growth media, etc.). Fragments of ketoreductase polypeptides (i.e., peptides) include fragments, preferably, having the same or equivalent function or activity as the full-length polypeptide. Both naturally occurring and recombinant forms of the *G. oxydans* 2-ketoreductase polypeptides or peptides may be used in the methods according to the present invention. Methods for directly isolating and purifying polypeptides or peptides from cellular or extracellular lysates are well known in the art (see E. L. V. Harris and S. Angal (Eds.), 1989, *Protein Purification Methods: A Practical Approach*, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof.

In addition, antibody-based methods can be used to isolate natural or recombinantly produced *G. oxydans* 2-ketoreductase polypeptides or peptides. Antibodies that recognize these polypeptides, or peptides derived therefrom, can be produced and isolated using methods known and practiced in the art (see below). *G. oxydans* 2-ketoreductase polypeptides or peptides can then be purified from a crude lysate by chromatography on antibody-conjugated solid-phase matrices (see E. Harlow and D. Lane, 1999, *Using Antibodies: A Laboratory Manual*, Cold Spring Harbor Laboratory, Cold Spring Harbor, N.Y.). Other isolation methods known and used in the art may also be employed.

To produce recombinant *G. oxydans* 2-ketoreductase polypeptides or peptides, DNA sequences encoding the polypeptides or peptides can be cloned into a suitable vector for expression in intact host cells or in cell-free translation systems as described above (see also J. Sambrook et al., 1989, *Molecular Cloning: A Laboratory Manual*, 2nd edition, Cold Spring Harbor Laboratory Press, Cold Spring Harbor, N.Y.). DNA sequences can be optimized, if desired, for more efficient expression in a given host organism. For example, codons can be altered to conform to the preferred codon usage in a given host cell or cell-free translation system using techniques routinely practiced in the art.

For some purposes, it may be preferable to produce *G. oxydans* 2-ketoreductase peptides or polypeptides in a recombinant system wherein the peptides or polypeptides carry additional sequence tags to facilitate purification. Such markers include epitope tags and protein tags. Non-limiting examples of epitope tags include c-myc, haemagglutinin (HA), polyhistidine (6X-HIS), GLU-GLU, and DYKD-DDDK (FLAG®; SEQ ID NO:3) epitope tags. Non-limiting examples of protein tags include glutathione-S-transferase (GST), green fluorescent protein (GFP), and maltose binding protein (MBP).

Epitope and protein tags can be added to peptides by a number of established methods. For example, DNA sequences encoding epitope tags can be inserted into protein-coding sequences as oligonucleotides or as primers used in PCR amplification. As an alternative, protein-coding sequences can be cloned into specific vectors that create fusions with epitope tags; for example, pRSET vectors (Invitrogen Corp., San Diego, Calif.). Similarly, protein tags can be added by cloning the coding sequence of a polypeptide or peptide into a vector that creates a fusion between the polypeptide or peptide and a protein tag of interest. Suitable vectors include, without limitation, the exemplary plasmids, pGEX (Amersham-Pharmacia Biotech, Inc., Piscataway, N.J.), pEGFP (CLONTECH Laboratories, Inc., Palo Alto, Calif.), and PMAL™ (New England BioLabs, Inc., Beverly, Mass.). Following expression, the epitope or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification.

In various embodiments, the recombinant *G. oxydans* 2-ketoreductase polypeptides are secreted to the cell surface, retained in the cytoplasm of the host cells, or secreted into the growth media. In each case, the production of *G. oxydans* 2-ketoreductase polypeptides can be established using anti-ketoreductase antibodies, or catalytic assays. The cell-surface and cytoplasmic recombinant *G. oxydans* 2-ketoreductase polypeptides can be isolated following cell lysis and extraction of cellular proteins, while the secreted recombinant *G. oxydans* 2-ketoreductase polypeptides can be isolated from the cell growth media by standard techniques (see I. M. Rosenberg (Ed.) 1996, *Protein Analysis and Purification: Benchtop Techniques*, Birkhauser, Boston, Cambridge, Mass.).

Methods to improve polypeptide production may include 1) the use of bacterial expressed fusion proteins comprising signal peptides or targeting sequences to promote secretion (Tessier et al., 1991, *Gene* 98:177–83; Garnier et al., 1995, *Biotechnology* 13:1101–4); 2) the use of serum-free and protein-free culture systems for economical polypeptide production (Zang et al., 1995, *Biotechnology* 13:389–92); 3) the use of the eukaryotic regulated secretory pathway for increased production and harvesting efficiency (see Chen et al., 1995, *Biotechnology* 13:1191–97). Polypeptide production may also be optimized by the utilization of a specific vector, host cell, expression system, or production protocol, as described in detail herein.

Large-scale microbial protein production can be achieved using well-established methods (see, e.g., W. Crueger and A. Crueger, 1990, *Biotechnology: A Textbook of Industrial Microbiology* Sinauer Associates, Sunderland, Mass.; A. N. Glazer and H. Nikaido, 1995, *Microbial biotechnology: fundamentals of applied microbiology* Freeman, New York, N.Y.; C. M. Brown et al., 1987, *Introduction to Biotechnology: Basic Microbiology*, Vol. 10, Blackwell, Oxford, UK). Methods for scaling-up baculovirus protein production can be found, for example, in R. L. Tom et al., 1995, *Methods Mol. Biol.* 39:203–24; R. L. Tom et al., 1995, *Appl. Microbiol. Biotechnol.* 44:53–8; S. A. Weiss, et al., 1995, *Methods Mol. Biol.* 39:79–95; and C. D. Richardson (Ed.) 1995, *Baculovirus Expression Protocols: Methods in Molecular Biology*, Vol. 39, Humana Press, Totowa, N.J. In additional, large-scale protein production services are commercially available from, e.g., PanVera Corp., Madison, Wis.; Oxford Expression Technologies, Oxford UK; BioXpress Laboratory, Athens, Ga.; and Recombinant Protein Expression Laboratory, Gainesville, Fla.

In general, large-scale microbial enzyme production systems employ the following procedures. Screens are used to test enzyme activity, pH optimum, temperature optimum, secretion (downstream processing), and the ability to grow the organism in inexpensive large-scale fermentation systems (high population densities from inexpensive carbon and nitrogen feedstocks, e.g., corn syrup, molasses, soybean meal, gluten, etc.). Strain improvements are created by random mutagenesis and screening or directed genetic manipulation (e.g., in *Bacillus, Streptomyces, Aspergillus* and *Saccharomyces* strains). For example, mutant strains can provide 1) relief of repression (e.g., catabolite repression); 2) increased promoter strength; 3) higher affinity ribosome-binding sites; 4) higher efficiency of mRNA leader translation; 5) increased mRNA half life; 6) increased translation efficiency through altered codon usage; 7) improvement of secretion efficiency; and 8) increased gene dosage (i.e., via chromosomal amplification or plasmid amplification). Process improvements are implemented by screening feeding strategies (e.g., batch, fed-batch, continuous, or recycle), reactor configurations, stirring methods (e.g., via impeller, bubble, air lift, packed bed, solid state, or hollow fiber), pH control, foam, and temperature. Enzymes produced by exemplary large-scale microbial systems include various serine proteinases, Zn metalloproteinases, aspartic proteinases, isomerases, pectinases, lipases, α-amylase, cellases, and glucomylases.

Uses for Polypeptides

The isolated *G. oxydans* 2-ketoreductase enzymes, and fragments modifications, and variants thereof, are useful for generating chiral alcohols for various biosynthetic or pharmaceutical applications. In various aspects, *G. oxydans* 2-ketoreductase can be used in reduction reactions involving ketones, especially alkylketones (e.g., 2-pentanone, 2-heptanone, 2-octanone, 2-decanone, and 2-hexanone. Such reactions can be used to produce, for example, 2-pentanol, 2-heptanol, 2-octanol, 2-decanol, and 2-hexanol. These chiral alcohols can be used as intermediates in synthetic reactions known in the art. In addition, 2-ketoreductase enzymes can be used in the synthesis of polyketides in conjunction with other enzymes, including dehydratase, acyl carrier protein, enoylreductase, 2-ketoacyl ACP synthase, and acyltransferase (see, e.g., M. McPherson et al., 1998, *J. Am. Chem. Soc.* 120, 3267–3268; U.S. Pat. No. 6,274,560 to Khosla et al.; U.S. Pat. No. 5,962,290 to Khosla et al.; U.S. Pat. No. 6,258,566 to Barr et al.).

In preferred embodiments, the products of reactions *G. oxydans* 2-ketoreductase are useful as intermediates for the synthesis of therapeutics or other beneficial compounds. For example, polyketides are useful as a large and diverse class of pharmaceutical products, including antibiotics (e.g., anthracyclines, tetracyclines, polyethers, ansamycins, macrolides of different types, such as polyenes and avermectins as well as classical macrolides such as erythromycins), anti-cancer agents (e.g., mithramycin, daunomycin, and dynemycin A), antifungals (e.g., griseofulvin and strobilurins), antiparasitics (e.g., avermectin and monensin), immunosuppressive agents (e.g., FK506 and rapamycin), cholesterol-lowering agents (lovastatin and squalestatins), and veterinary products (e.g., monensin and avermectin).

For use in medical or industrial applications, G. oxydans 2-ketoreductase enzymes, fragments, modifications, or variants thereof can be added to a particular chemical reaction by any available means. For example, 2-ketoreductase isolated from natural (e.g., Gluconobacter oxydans cells), recombinant, or synthetic sources may be used. Alternatively, cell extracts or whole cells expressing a secreted form of G. oxydans 2-ketoreductase may be used. Different sources of G. oxydans 2-ketoreductase can be compared to determine the enzyme source that results in, for example, the highest yields of product or the lowest production costs.

Antibodies

Another aspect of the invention pertains to antibodies directed to G. oxydans 2-ketoreductase polypeptides, or fragments or variants thereof. The invention provides polyclonal and monoclonal antibodies that bind ketoreductase or ketoreductase fragments. The antibodies may be elicited in an animal host (e.g., non-human mammal) by immunization with enzyme components. Antibodies may also be elicited by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including $Fab_1$ and $Fab(ab)_2$ fragments of antibodies.

In accordance with the present invention, antibodies are directed to a G. oxydans 2-ketoreductase polypeptide (e.g., SEQ ID NO:2), or variants, or fragments thereof. For example, antibodies can be produced to bind to G. oxydans 2-ketoreductase polypeptide encoded by an alternate splice variant or SNP variant of SEQ ID NO:1. An isolated G. oxydans 2-ketoreductase (e.g., SEQ ID NO:2), or variant, or fragment thereof, can be used as an immunogen to generate antibodies using standard techniques for polyclonal and monoclonal antibody preparation. A full-length G. oxydans 2-ketoreductase polypeptide can be used or, alternatively, the invention provides antigenic peptide portions of the polypeptide for use as immunogens. An antigenic peptide comprises at least 5 contiguous amino acid residues, preferably at least 12 contiguous amino acid residues, of the amino acid sequence shown in SEQ ID NO:2, or a variant thereof, and encompasses an epitope of a G. oxydans 2-ketoreductase polypeptide such that an antibody raised against the peptide forms a specific immune complex with a G. oxydans 2-ketoreductase sequence.

An appropriate immunogenic preparation can contain, for example, recombinantly produced G. oxydans 2-ketoreductase polypeptide or a chemically synthesized polypeptide, or fragments thereof. The preparation can further include an adjuvant, such as Freund's complete or incomplete adjuvant, or similar immunostimulatory agent. A number of adjuvants are known and used by those skilled in the art. Non-limiting examples of suitable adjuvants include incomplete Freund's adjuvant, mineral gels such as alum, aluminum phosphate, aluminum hydroxide, aluminum silica, and surface-active substances such as lysolecithin, pluronic polyols, polyanions, peptides, oil emulsions, keyhole limpet hemocyanin, and dinitrophenol. Further examples of adjuvants include N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-Lalanyl-D-isoglutaminyl-L-alanine-2-(1'-2'-dipalmitoyl-sn-glycero-3 hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. A particularly useful adjuvant comprises 5% (wt/vol) squalene, 2.5% Pluronic L121 polymer and 0.2% polysorbate in phosphate buffered saline (Kwak et al., 1992, New Eng. J. Med. 327:1209–1215). Preferred adjuvants include complete BCG, Detox, (RIBI, Immunochem Research Inc.), ISCOMS, and aluminum hydroxide adjuvant (Superphos, Biosector). The effectiveness of an adjuvant may be determined by measuring the amount of antibodies directed against the immunogenic peptide.

Polyclonal antibodies to G. oxydans 2-ketoreductase polypeptides or peptides can be prepared as described above by immunizing a suitable subject (e.g., horse, donkey, goat, rabbit, rat, mouse, chicken, or other non-human animal) with a ketoreductase immunogen. The antibody titer in the immunized subject can be monitored over time by standard techniques, such as with an enzyme linked immunosorbent assay (ELISA) using immobilized G. oxydans 2-ketoreductase polypeptide or peptide. If desired, the antibody molecules can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique (see Kohler and Milstein, 1975, Nature 256:495–497; Brown et al., 1981, J. Immunol. 127:539–46; Brown et al., 1980, J. Biol. Chem. 255:4980–83; Yeh et al., 1976, PNAS 76:2927–31; and Yeh et al., 1982, Int. J. Cancer 29:269–75), the human B cell hybridoma technique (Kozbor et al., 1983, Immunol. Today 4:72), the EBV-hybridoma technique (Cole et al., 1985, Monoclonal Antibodies and Cancer Therapy, Alan R. Liss, Inc., pp. 77–96) or trioma techniques.

The technology for producing hybridomas is well-known (see generally R. H. Kenneth, 1980, Monoclonal Antibodies: A New Dimension In Biological Analyses, Plenum Publishing Corp., New York, N.Y.; E. A. Lerner, 1981, Yale J. Biol. Med., 54:387–402; M. L. Gefter et al., 1977, Somatic Cell Genet. 3:231–36). In general, an immortal cell line (typically a myeloma) is fused to lymphocytes (typically splenocytes) from a mammal immunized with a G. oxydans 2-ketoreductase immunogen as described above, and the culture supernatants of the resulting hybridoma cells are screened to identify a hybridoma producing a monoclonal antibody that binds G. oxydans 2-ketoreductase polypeptides or peptides.

Any of the many well known protocols used for fusing lymphocytes and immortalized cell lines can be applied for the purpose of generating an monoclonal antibody to a *G. oxydans* 2-ketoreductase (see, e.g., G. Galfre et al., 1977, *Nature* 266:55052; Gefter et al., 1977; Lerner, 1981; Kenneth, 1980). Moreover, the ordinarily skilled worker will appreciate that there are many variations of such methods. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin, and thymidine (HAT medium). Any of a number of myeloma cell lines can be used as a fusion partner according to standard techniques, e.g., the P3-NS1/1-Ag4-1, P3-x63-Ag8.653, or Sp2/O-Ag14 myeloma lines. These myeloma lines are available from ATCC (American Type Culture Collection, Manassas, Va.). Typically, HAT-sensitive mouse myeloma cells are fused to mouse splenocytes using polyethylene glycol (PEG). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind *G. oxydans* 2-ketoreductase polypeptides or peptides, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the corresponding *G. oxydans* 2-ketoreductase polypeptide to thereby isolate immunoglobulin library members that bind the polypeptide. Kits for generating and screening phage display libraries are commercially available (e.g., the Pharmacia Recombinant Phage Antibody System; and the Stratagene SurfZAP™ Phage Display Kit).

Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al., 1991, *Bio/Technology* 9:1370–1372; Hay et al., 1992, *Hum. Antibod. Hybridomas* 3:81–85; Huse et al., 1989, *Science* 246:1275–1281; Griffiths et al., 1993, *EMBO J.* 12:725–734; Hawkins et al., 1992, *J. Mol. Biol.* 226:889–896; Clarkson et al., 1991, *Nature* 352:624–628; Gram et al., 1992, *PNAS* 89:3576–3580; Garrad et al., 1991, *Bio/Technology* 9:1373–1377; Hoogenboom et al., 1991, *Nuc. Acid Res.* 19:4133–4137; Barbas et al., 1991, *PNAS* 88:7978–7982; and McCafferty et al., 1990, *Nature* 348:552–55.

Additionally, recombinant antibodies to a *G. oxydans* 2-ketoreductase polypeptide, such as chimeric monoclonal antibodies, can be made using standard recombinant DNA techniques. Such chimeric monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., 1988, *Science* 240:1041–1043; Liu et al., 1987, *PNAS* 84:3439–3443; Liu et al., 1987, *J. Immunol.* 139:3521–3526; Sun et al., 1987, *PNAS* 84:214–218; Nishimura et al., 1987, *Canc. Res.* 47:999–1005; Wood et al., 1985, *Nature* 314:446–449; and Shaw et al., 1988, *J. Natl. Cancer Inst.* 80:1553–1559; S. L. Morrison, 1985, *Science* 229:1202–1207; Oi et al., 1986, *BioTechniques* 4:214; Winter U.S. Pat. No. 5,225,539; Jones et al., 1986, *Nature* 321:552–525; Verhoeyan et al., 1988, *Science* 239:1534; and Bcidler et al., 1988, *J. Immunol.* 141:4053–4060.

An antibody against a *G. oxydans* 2-ketoreductase (e.g., monoclonal antibody) can be used to isolate the corresponding enzyme or enzyme fragment by standard techniques, such as affinity chromatography or immunoprecipitation. For example, antibodies can facilitate the purification of a natural *G. oxydans* 2-ketoreductase from cells and of a recombinantly produced *G. oxydans* 2-ketoreductase or enzyme fragment expressed in host cells. In addition, an antibody that binds to a *G. oxydans* 2-ketoreductase polypeptide can be used to detect the corresponding enzyme (e.g., in a cell, cellular lysate, or cell supernatant) in order to evaluate the abundance, localization, or pattern of expression of the protein. Detection methods employing antibodies include well-established techniques, such as Western blot, dot blot, colony blot, ELISA, immunocytochemical, and immunohistochemical analysis.

Modulators

The *G. oxydans* 2-ketoreductase, polynucleotides, variants, or fragments thereof, can be used to screen for test agents (e.g., agonists, antagonists, or inhibitors) that modulate the levels or activity of the corresponding enzyme. In addition, these ketoreductase molecules can be used to identify endogenous modulators that bind to polypeptides or polynucleotides in the *G. oxydans* cell. In one aspect of the present invention, the full-length *G. oxydans* 2-ketoreductase (e.g., SEQ ID NO:2) is used to identify modulators. Alternatively, variants or fragments of a *G. oxydans* 2-ketoreductase are used. Such fragments may comprise, for example, one or more domains of a *G. oxydans* 2-ketoreductase (e.g., the short chain dehydrogenase domain) disclosed herein. A wide variety of assays may be used for these screens, including in vitro protein-protein binding assays, electrophoretic mobility shift assays, immunoassays, and the like.

The term "modulator" as used herein describes any test agent, molecule, protein, peptide, or compound with the capability of directly or indirectly altering the physiological function, stability, or levels of *G. oxydans* 2-ketoreductase. Modulators that bind to the *G. oxydans* 2-ketoreductase polypeptides or polynucleotides of the invention are potentially useful in biotechnology or pharmaceutical applications, as described in detail herein. Test agents useful as modulators may encompass numerous chemical classes, though typically they are organic molecules, preferably small organic compounds having a molecular weight of more than 50 and less than about 2,500 daltons. Such molecules can comprise functional groups necessary for structural interaction with proteins, particularly hydrogen bonding, and typically include at least an amine, carbonyl, hydroxyl or carboxyl group, preferably at least two of the functional chemical groups. Test agents which can be used as modulators often comprise cyclical carbon or heterocyclic structures and/or aromatic or polyaromatic structures substituted with one or more of the above functional groups. Test agents can also comprise biomolecules including peptides, saccharides, fatty acids, steroids, purines, pyrimidines, derivatives, structural analogs, or combinations thereof.

Test agents finding use as modulators may include, for example, 1) peptides such as soluble peptides, including Ig-tailed fusion peptides and members of random peptide libraries (see, e.g., Lam et al., 1991, *Nature* 354:82–84; Houghten et al., 1991, *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al, (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules.

Test agents and modulators can be obtained from a wide variety of sources including libraries of synthetic or natural compounds. Synthetic compound libraries are commercially available from, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Natural compound libraries comprising bacterial, fungal, plant or animal extracts are available from, for example, Pan Laboratories (Bothell, Wash.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carell et al., 1994, *Angew. Chem. Int. Ed. Engl.* 33:2059; Carell et al., 1994, *Angew. Chem. Int. Ed. Engl.* 33:2061; and in Gallop et al., 1994, *J. Med. Chem.* 37:1233). In addition, natural or synthetic compound libraries and compounds can be readily modified through conventional chemical, physical and biochemical means (see, e.g., Blondelle et al., 1996, *Trends in Biotech.* 14:60), and may be used to produce combinatorial libraries. In another approach, previously identified pharmacological agents can be subjected to directed or random chemical modifications, such as acylation, alkylation, esterification, amidification, and the analogs can be screened for 2-ketoreductase-modulating activity.

Numerous methods for producing combinatorial libraries are known in the art, including those involving biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer, or small molecule libraries of compounds (K. S. Lam, 1997, *Anticancer Drug Des.* 12:145).

Libraries may be screened in solution (e.g., Houghten, 1992, *Biotechniques* 13:412–421), or on beads (Lam, 1991 *Nature* 354:82–84), chips (Fodor, 1993 *Nature* 364:555–556), bacteria or spores (Ladner U.S. Pat. No. 5,223,409), plasmids (Cull et al., 1992 Proc. Natl. Acad. Sci. USA 89:1865–1869), or on phage (Scott and Smith, 1990, *Science* 249:386–390; Devin, 1990, *Science* 249:404–406; Cwirla et al., 1990, *Proc. Natl. Acad. Sci. USA* 97:6378–6382; Felici, 1991, *J. Mol. Biol.* 222:301–310; Ladner, supra).

Where the screening assay is a binding assay, a *G. oxydans* 2-ketoreductase polypeptide, polynucleotide, functional equivalent, or fragment thereof, may be joined to a label, where the label can directly or indirectly provide a detectable signal. Various labels include radioisotopes, fluorescers, chemiluminescers, enzymes, specific binding molecules, particles, e.g. magnetic particles, and the like. Preferred fluorescent labels include, for example, Cy3, Cy5, GFP (e.g., EGFP, DsRed, dEFP, etc. (CLONTECH, Palo Alto, Calif.)), Alexa, BODIPY, fluorescein (e.g., FluorX, DTAF, and FITC), rhodamine (e.g., TRITC), auramine, Texas Red, AMCA blue, and Lucifer Yellow. Preferred isotope labels include $^3$H, $^{14}$C, 32 P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Non-limiting examples of enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), and digoxin/anti-digoxin, are known in the art, and are commercially available (see, e.g., ABC kit, Vector Laboratories, Inc., Burlingame, Calif.; NEN® Life Science Products, Inc., Boston, Mass.). For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc., that are used to facilitate optimal protein-protein binding and/or reduce non-specific or background interactions. Reagents that improve the efficiency of the assay, such as protease inhibitors, nuclease inhibitors, anti-microbial agents, etc., may be used. The components are added in any order that produces the requisite binding. Incubations are performed at any temperature that facilitates optimal activity, typically between 4° and 40° C. Incubation periods are selected for optimum activity, but may also be optimized to facilitate rapid high-throughput screening. Normally, between 0.1 and 1 hr will be sufficient. In general, a plurality of assay mixtures is run in parallel with different agent concentrations to obtain a differential response to these concentrations. Typically, one of these concentrations serves as a negative control, i.e. at zero concentration or below the level of detection.

To perform cell-free screening assays, it may be desirable to immobilize either the a *G. oxydans* 2-ketoreductase polypeptide, polynucleotide, variant, or fragment to a surface to facilitate identification of modulators that bind to these molecules, as well as to accommodate automation of the assay. For example, a fusion protein comprising a *G. oxydans* 2-ketoreductase polypeptide and an affinity-tag can be produced as described in detail herein. In one embodiment, a GST-fusion protein comprising a *G. oxydans* 2-ketoreductase polypeptide is adsorbed onto glutathione sepharose beads (Sigma Chemical, St. Louis, Mo.) or glutathione-derivatized microtiter plates. Cell lysates (e.g., containing $^{35}$S labeled polypeptides) are added to the polypeptide-coated beads under conditions to allow complex formation (e.g., at physiological conditions for salt and pH). Following incubation, the polypeptide-coated beads are washed to remove any unbound polypeptides, and the amount of immobilized radiolabel is determined. Alternatively, the complex is dissociated and the radiolabel present in the supernatant is determined. In another approach, the beads are analyzed by SDS-PAGE to identify ketoreductase-binding polypeptides.

Various binding assays can be used to identify modulators that alter the function or levels of *G. oxydans* 2-ketoreductase. Such assays are designed to detect the interaction of test agents with *G. oxydans* 2-ketoreductase polypeptides, polynucleotides, variants, or fragments thereof. Interactions may be detected by direct measurement of binding. Non-limiting examples of useful binding assays are detailed as follows. Modulators that bind to *G. oxydans* 2-ketoreductase polypeptides, polynucleotides, functional equivalents, or fragments thereof, can be identified using real-time Bimolecular Interaction Analysis (BIA; Sjolander et al., 1991, *Anal. Chem.* 63:2338–2345; Szabo et al., 1995, *Curr. Opin. Struct. Biol.* 5:699–705; e.g., BIAcore™; LKB Pharmacia, Sweden). Modulators can also be identified by scintillation proximity assays (SPA, described in U.S. Pat. No. 4,568,649). Binding assays using mitochondrial targeting signals (Hurt et al., 1985, *EMBO J.* 4:2061–2068; Eilers and Schatz, 1986, *Nature* 322:228–231) a plurality of defined polymers synthesized on a solid substrate (Fodor et al., 1991, *Science* 251:767–773) may also be employed.

Two-hybrid systems may be used to identify modulators (see, e.g., U.S. Pat. No. 5,283,317; Zervos et al., 1993, *Cell* 72:223–232; Madura et al., 1993, *J. Biol. Chem.* 268:12046–12054; Bartel et al., 1993, *Biotechniques* 14:920–924; Iwabuchi et al., 1993, *Oncogene* 8:1693–1696; and Brent WO 94/10300). Alternatively, three-hybrid (Licitra et al., 1996, *Proc. Natl. Acad. Sci. USA* 93:12817–12821), and reverse two-hybrid (Vidal et al., 1996, *Proc. Natl. Acad. Sci. USA* 93:10315–10320) systems may be used. Commercially available two-hybrid systems such as the CLONTECH Matchmaker™ systems and protocols (CLONTECH Laboratories, Inc., Palo Alto, Calif.) are also useful (see also, A. R. Mendelsohn et al., 1994, *Curr. Op. Biotech.* 5:482; E. M. Phizicky et al., 1995, *Microbiological Rev.* 59:94; M. Yang et al., 1995, *Nucleic Acids Res.* 23:1152; S. Fields et al., 1994, *Trends Genet.* 10:286; and U.S. Pat. Nos. 6,283,173 and 5,468,614).

Several methods of automated assays have been developed in recent years so as to permit screening of tens of thousands of test agents in a short period of time. High-throughput screening methods are particularly preferred for use with the present invention. The binding assays described herein can be adapted for high-throughput screens, or alternative screens may be employed. For example, continuous format high throughput screens (CF-HTS) using at least one porous matrix allows the researcher to test large numbers of test agents for a wide range of biological or biochemical activity (see U.S. Pat. No. 5,976,813 to Beutel et al.). Moreover, CF-HTS can be used to perform multi-step assays.

Alternatively, interactions with test agents may be detected by indirect indicators of binding, such as stabilization/destabilization of protein structure, or activation/inhibition of biological function. For example, modulating agents may be identified by an increase or decrease in levels of chiral alcohol produced by *G. oxydans* 2-ketoreductase upon incubation with substrate. Specifically, agonist agents would be expected to increase alcohol levels, whereas antagonist agents would be expected to decrease alcohol levels produced by the enzyme.

In one embodiment of the present invention, an agonist or antagonist is identified by incubating the disclosed *G. oxydans* 2-ketoreductase, or fragments or variants thereof, with a test agent. The *G. oxydans* 2-ketoreductase may be expressed by host cells, or may be isolated therefrom. The *G. oxydans* 2-ketoreductase and test agent is incubated with substrate, and levels of alcohol product are determined and compared with standard levels. Increased levels of alcohol indicate identification of an agonist agent, while decreased levels of alcohol indicate identification of an antagonist agent.

Embodiments

This invention encompasses, but is not limited to, the following embodiments:

An isolated nucleic acid comprising a nucleotide sequence encoding amino acid sequence SEQ ID NO:2.

An isolated nucleic acid comprising a nucleotide sequence encoding at least 12 contiguous residues of amino acid sequence SEQ ID NO:2.

An isolated nucleic acid comprising a nucleotide sequence encoding at least 12 contiguous residues of the short chain dehydrogenase domain of amino acid sequence SEQ ID NO:2.

An isolated nucleic acid comprising nucleotide sequence SEQ ID NO:1.

An isolated nucleic acid comprising at least 21 contiguous nucleotides of nucleotide sequence SEQ ID NO:1.

An isolated nucleic acid comprising a nucleotide sequence which is at least 54% identical to nucleotide sequence SEQ ID NO:1.

An isolated nucleic acid comprising a nucleotide sequence which is complementary to a nucleotide sequence of the invention (above).

A vector comprising an isolated nucleic acid of the invention (above).

A host cell comprising a vector of the invention (above), wherein the host cell is selected from the group consisting of bacterial, fungal, insect, mammalian, and plant cells.

The bacterial host cell of the invention (above), wherein the bacterial host cell is selected from the group consisting of *Escherichia coli, Staphlococcus aureus, Bacillus licheniformis, Bacillus amyloliquefaciens, Bacillus subtilis, Streptomyces lividans*, and *Streptomyces coelicolor*.

A probe comprising an isolated nucleic acid of the invention (above). In specific aspects, the probe may comprise a nucleotide sequence selected from the group consisting of SEQ ID NO:9–SEQ ID NO:10.

A primer comprising an isolated nucleic acid of the invention (above). In specific aspects, the primer may comprise a nucleotide sequence selected from the group consisting of SEQ ID NO:9–SEQ ID NO:10.

An isolated polypeptide (e.g., recombinant polypeptide) comprising amino acid sequence SEQ ID NO:2.

An isolated polypeptide (e.g., recombinant polypeptide) comprising at least 12 contiguous residues of amino acid sequence SEQ ID NO:2.

An isolated polypeptide (e.g., recombinant polypeptide) comprising at least 12 contiguous residues of the short chain dehydrogenase domain of amino acid sequence SEQ ID NO:2. An isolated polypeptide (e.g., recombinant polypeptide) comprising an amino acid sequence which is at least 54% identical to amino acid sequence SEQ ID NO:2.

An antibody which binds to an isolated polypeptide of the invention (above). In one aspect, the antibody may be monoclonal.

A kit for detecting a nucleic acid comprising:
  a) the a probe of the invention (above); and
  b) at least one component to detect binding of the probe to a nucleic acid.

A kit for detecting an amino acid sequence comprising:
  a) an antibody of the invention (above); and
  b) at least one component to detect binding of the antibody to an amino acid sequence.

A method for detecting a nucleic acid comprising:
  a) incubating a probe of the invention (above) with a biological sample comprising nucleic acids, thereby forming a hybridization complex; and
  b) detecting the complex formed in (a), wherein the presence of the complex indicates detection of a nucleic acid.

A method for detecting a polypeptide comprising:
  a) incubating an antibody of the invention (above) with a biological sample comprising polypeptides, thereby forming a complex; and
  b) detecting the complex formed in (a), wherein the presence of the complex indicates detection of a polypeptide.

A method for detecting a binding factor comprising:
  a) incubating an isolated nucleic acid of the invention (above) with a test agent, thereby forming a complex; and
  b) detecting the complex formed in (a), wherein the presence of the complex indicates detection of a binding factor.

A method for detecting a binding factor comprising:
  a) incubating an isolated polypeptide of the invention (above) with a test agent, thereby forming a complex; and
  b) detecting the complex formed in (a), wherein the presence of the complex indicates detection of a binding factor.

A method for producing a recombinant polypeptide comprising:
  a) culturing a host cell of the invention (above) under conditions suitable for the production of a recombinant polypeptide; and
  b) recovering the recombinant polypeptide from the host cell or host cell culture, thereby producing the recombinant polypeptide.

A method for producing a recombinant polypeptide comprising:
  a) culturing a bacterial host cell of the invention (above) under conditions suitable for the expression of a recombinant polypeptide; and
  b) recovering the recombinant polypeptide from the host cell or host cell culture, thereby producing the recombinant polypeptide.

A method of isolating a recombinant polypeptide comprising:
  a) incubating a biological sample obtained from a host cell expressing recombinant polypeptide comprising amino acid sequence SEQ ID NO:2 with an antibody of the invention (above), thereby forming a complex; and
  b) recovering a polypeptide from the complex, thereby isolating the polypeptide.

A method of producing a chiral alcohol comprising: incubating an isolated polypeptide of the invention (above) with a ketone substrate under conditions to allow reduction of the ketone substrate, thereby producing a chiral alcohol. In one aspect, the ketone substrate is an alkylketone. In various aspects, the alkylketone is selected from the group consisting of 2-pentanone, 2-heptanone, 2-octanone, 2-decanone, and 2-hexanone.

A method for detecting an agonist agent comprising:
  a) incubating a host cell of the invention (above), with a test agent and a ketone substrate under conditions to allow reduction of the ketone substrate and production of alcohol;
  b) measuring levels of alcohol, produced in step (a); and
  c) comparing the levels determined in step (b) to levels produced in the absence of the test agent, wherein an increase in levels indicates detection of an agonist agent. In one aspect, the ketone substrate is an alkylketone. In various aspects, the alkylketone is selected from the group consisting of 2-pentanone, 2-heptanone, 2-octanone, 2-decanone, and 2-hexanone.

A method for detecting an agonist agent comprising:
  a) incubating a bacterial host cell of the invention (above) with a test agent and a ketone substrate under conditions to allow reduction of the ketone substrate and production of alcohol;
  b) measuring levels of alcohol produced in step (a); and
  c) comparing the levels determined in step (b) to levels produced in the absence of the test agent, wherein an increase in levels indicates detection of an agonist agent. In one aspect, the ketone substrate is an alkylketone. In various aspects, the alkylketone is selected from the group consisting of 2-pentanone, 2-heptanone, 2-octanone, 2-decanone, and 2-hexanone.

A method for detecting an agonist agent comprising:
  a) incubating an isolated polypeptide of the invention (above) with a test agent and a ketone substrate under conditions to allow reduction of the ketone substrate and production of alcohol;
  b) measuring levels of alcohol produced in step (a); and
  c) comparing the levels determined in step (b) to levels produced in the absence of the test agent, wherein an increase in levels indicates detection of an agonist agent. In one aspect, the ketone substrate is an alkylketone. In various aspects, the alkylketone is selected from the group consisting of 2-pentanone, 2-heptanone, 2-octanone, 2-decanone, and 2-hexanone.

An American Type Culture Collection deposit deposited as ATCC Accession No. PTA-3864.

A nucleic acid consisting of the nucleotide sequence deposited as ATCC Accession No. PTA-3864.

A recombinant polypeptide encoded by the nucleotide sequence deposited as ATCC Accession No. PTA-3864.

EXAMPLES

The examples as set forth herein are meant to exemplify the various aspects of the present invention and are not intended to limit the invention in any way.

Example 1

Purification of G. oxydans 2-Ketoreductase

Fermentation: *Gluconobacter oxydans* (SC13851) was grown on a glycerol-containing medium as follows. Cultures were grown in 500 ml Erlenmeyer flasks for 24 hr in 100 ml medium A (5% glycerol, 0.5% yeast extract, 0.05% ammonium sulfate, 0.3% peptone, 0.05% $K_2HPO_4$, 0.02% $MgSO_4.7H_2O$, 0.001% NaCl, 0.001% $FeSO_4.7H_2O$, and 0.001% $MnSO_4.7H_2O$). After 24 hr, the flask cultures were used to inoculate (1% v/v inoculum) a 15 L fermentor containing medium A. The fermentation was carried out at 28° C. for 24 hr. A 4000 L fermentor (Expend Industries, Inc., Brooklyn, N.Y.) was inoculated with 10 L inoculum from the 15 L fermentor. The 4000 L fermentor contained medium A with 0.05% antifoam SAG 5693. The fermentor was operated at 28° C., 100 LPM airflow, 690 mbar pressure, and 620 rpm agitation for 48 hr.

Cell recovery: The fermentor broth was cooled to 8° C. at the harvest. The tank was pressurized to 15 psig and broth was diverted to a Sharples (Alfa Laval Separation, Inc., Warminster, Pa.) centrifuge running at 18,000×g. The broth was processed at 3.2 L/min and recovered cells were stored at −70° C. until further use.

Purification of 2-ketoreductase: All the purification steps were carried out at 4° C. Forty-four grams of cells were suspended in 0.3 L buffer A (50 mM Tris-HCl, pH 7.5, 1 mM $CaCl_2$, and 1 mM $MgCl_2$). After 30 min of homogenization, the cell suspension was passed through a microfluidizer (Microfludics International Corporation, Newton, Mass.) twice at 12,000 psi. The supernatant obtained by centrifugation (at 30,000×g for 30 min) was loaded onto DEAE cellulose column (400 ml) (Whatman, Maidstone, England), which was pre-equilibrated with buffer A. The enzyme activity was eluted with a 0 to 0.8 M NaCl gradient in buffer A.

The active fractions were pooled, and ammonium sulfate at 132 g/L was added before loading onto a phenylsepharose column (350 ml), which was pre-equilibrated with buffer A containing 1 M ammonium sulfate. The column was then washed with buffer A containing 1 M ammonium sulfate and the enzyme was eluted with a 1 M to 0 M ammonium sulfate gradient (total volume, 1.2 L). The fractions containing the active enzyme were pooled (150 ml) and concentrated with an Amicon YM-30 membrane (Amicon, Beverly, Mass.) to 8 ml.

The enzyme was then loaded onto a Sephacryl S-200 gel-filtration column (400 ml column) (Pharmacia, Piscataway, N.J.). The enzyme was eluted with buffer A containing 0.1 M NaCl with a flow rate of 0.8 ml/min. The active fractions from the gel-filtration column were pooled, and then loaded onto a mono Q ion-exchange (BioRad Q2) column (Bio-Rad, Hercules, Calif.). The enzyme activity was eluted with a 0 to 0.8 M NaCl gradient in buffer A.

The fractions containing the active enzyme were pooled (5.6 ml) and concentrated with a Centricon-30 membrane to 0.6 ml. The enzyme was then loaded onto a Superdex-75 gel-filtration column (FPLC; Pharmacia) and eluted with buffer A containing 0.1 M NaCl. The enzyme present in fraction 14 was analyzed by sodium dodecyl sulfate-polyacrylamide (SDS-PAGE) electrophoresis. This analysis indicated that the enzyme was present as a single band on the gel with a calculated molecular weight of 29 kilodaltons.

Example 2

Analysis of Purified G. oxydans 2-Ketoreductase

Protein assay: The Bio-Rad protein assay was used to determine protein concentration. The assay was performed according to the manufacturer's protocol (Bio-Rad). Samples containing 1–10 µl of enzyme fraction were brought to a volume of 0.8 ml with water. Next, 0.2 ml of the Bio-Rad reagent was added to the 0.8 ml sample solution. This was mixed thoroughly. The absorbance of the solution was measured at 595 nm. The protein concentration (mg/ml) was calculated from the standard curve using bovine serum albumin as standard protein.

Enzyme activity units: One unit (U) of enzyme activity was defined as one micromole of S-2-pentanol formed in 1 hr under the conditions described above. Results from the protein analysis of *G. oxydans* 2-ketoreductase are summarized below.

TABLE 1

| Steps | Volume (mL) | Enzyme Activity (Units) | Protein (mg) | Sp.Activity (Units/mg) | S-2-Pentanol (e e) | Purification Fold |
|---|---|---|---|---|---|---|
| Cell extract | 300 | 390.00 | 729.00 | 0.50 | | 1.00 |
| DEAE Cellulose | 180 | 235.80 | 185.40 | 1.27 | | 25.40 |
| Phenylsepharose | 150 | 186.00 | 72.00 | 2.58 | | 51.60 |
| Amicon concentration | 10 | | | | | |
| Sephacryl S200 Gel filtratio | 22 | 27.28 | 4.40 | 6.20 | >99 | 124.00 |
| Mono Q column | 5.6 | 35.39 | 3.64 | 9.72 | | 194.40 |
| Centricon concentration | 0.25 | | | | | |
| Sephadex-75 Gel filtration | 0.75 | 13.28 | 0.90 | 14.76 | >99 | 295.20 |

2-Pentanone reduction assays were carried out using both resting cells and the cell extract (soluble enzyme) of *Gluconobacter oxydans*.

Whole cell assays: Three grams of wet cell paste were suspended in 15 ml buffer containing 0.1 M Tris-HCl, pH 8, and 5 mM EDTA. The cell suspension was treated with 0.36 ml toluene. The treated cell suspension was shaken gently for 30 min in a 50 ml Erlenmeyer flask. The cells were then collected by centrifuging at 18,000×g for 20 minutes. Toluene treated cells (0.25 g) were suspended in 10 ml of 0.2 M Tris-HCl buffer pH 7.5, containing 10 mM $CaCl_2$ and 10 mM $MgCl_2$ in a 25 ml Teflon® flask. The following components were added to the reaction mixture: 7 mg $NAD^+$, 0.136 g sodium formate, 1.5 U formate dehydrogenase, and 0.025 ml 2-pentanone (Sigma, St. Louis, Mo.). The reaction mixture in the flask was incubated in a shaker at 28° C. with agitation at 200 rpm. At various time points (2–18 hr), samples containing 0.5 ml of reaction mixture were removed, and 2 ml of ethyl acetate was added to each sample to stop the reaction. The organic layer was separated by centrifugation and was used to analyze both the substrate and product.

Soluble enzyme assays: Samples of the enzyme were incubated in a reaction mixture (5 ml) containing 0.35 mg $NAD^+$, 68 mg sodium formate, 0.75 U formate dehydrogenase, and 5 mg 2-pentanone. Reactions were carried out in a Teflon® flask at 28° C. on a shaker at 200 rpm. After 18 hr, the reactions were quenched with 10 ml of ethyl acetate and analyzed by gas chromatography.

Analysis of enantiomeric alcohols by gas chromatography: Samples were extracted in ethyl acetate and dried over anhydrous magnesium sulfate. Samples were then applied onto a Astec Chiraldex G-TA, gamma cyclodextrin column (20 m×0.25 mm×0.125 µm thickness; Astec, Whippany, N.J.) equipped with a guard column (Hewlett-Packard Ultra II, 5% phenyl methyl silicone, 5 m×0.32 mm×0.17 µm thickness; Agilent Technologies, Palo Alto, Calif.). The temperature of the injector was set at 150° C. and the detector of the chromatograph (Hewlett-Packard 5890) was set at 200° C. Detection was carried out with a flame ionization detector (Agilent Technologies). The separation was carried out by a gradient under the following conditions: 28° C. for 15 minutes, 5° C./min to 50° C. and hold 5 minutes. The helium flow rate was maintained at 22 cm/min. Under these conditions, the retention times for S-2-pentanol, R-2-pentanol, and 2-pentanone were 10.85, 11.67 and 17.84 minutes respectively.

Peptide Sequencing of the purified 2-ketoreductase: The purified protein was sent for N-terminal and internal peptide sequences to Argo BioAnalytica, Inc., Morris Plains, N.J. The following are the sequences obtained for the 2-ketoreductase.

N-Terminal Sequence
$NH_2$-Ser-Leu-Ser-Gly-Lys-Ile-Ala-Ala-Val-Thr-Gly-Ala-Ala-Gln-Gly-COOH (SEQ ID NO:4).

Internal Peptides
Peptide 1: $NH_2$-Lys-Arg-Met-Ala-Glu-Ile-Thr-Gly-Thr-Glu-Ile-COOH (SEQ ID NO:5); and Peptide 2: $NH_2$-Lys-Val-Glu-Ala-Leu-Gly-Arg-Arg-Ala-Val-COOH (SEQ ID NO:6).

Example 3

Identification of the 2-Ketoreductase Gene

*Gluconobacter oxydans* (BMS Collection No. SC13851; ATCC No. 621) was grown in 50 ml LB medium (1% tryptone, 0.5% yeast extract, 0.5% NaCl) at 37° C. for 16 hr at 200 rpm in a shaker. The cells were harvested by centrifugation and the chromosomal DNA was prepared (see Ausubel et al. (Eds.), 1981, *Current Protocols in Molecular Biology*, vol. 2, section 13.11.2, John Wiley and Sons, New York). Degenerate PCR primers based on internal peptides (oligo GO1: 5'-AAR GTI GAR GCI YTI GGI MGI MGI GCI GT-3'; SEQ ID NO:7) (oligo GO4: 5'-ATY TCI GTI CCI GTI ATY TCI GCC AT-3'; SEQ ID NO:8), where "Y"=C+T; "R"=A+G; "I"=deoxyinosine; and "M"=A+C), were used to amplify the gene using genomic DNA as template. The amplification conditions included incubation at 94° C. for 1 min, followed by 30 cycles at 94° C. for 0.5 min; 50° C. for 0.5 min; and 72° C. for 0.5 min using a Hybaid PCR Express thermocycler (ThermoHybaid US, Franklin, Mass.). The PCR fragments were electrophoresed at 60 V for 2 hr through a 0.8% agarose gel in TAE buffer (0.04 M Trizma base, 0.02 M acetic acid, and 0.001 M EDTA, pH 8.3) containing 0.5 µg/ml ethidium bromide. The 400 bp PCR Fragment was identified by comparison to a 1 kb Plus DNA ladder (Invitrogen) and excised using a scalpel. The DNA was isolated from the agarose using the QIAquick Gel Extraction Kit (QIAGEN, Chatsworth, Calif.). The resulting 400 base pair (bp) PCR fragment was cloned into pCR2.1™ using the TA Cloning kit (Invitrogen, Carlsbad, Calif.).

To isolate the complete 2-ketoreductase gene, *G. oxydans* chromosomal DNA was cleaved with restriction endonucleases BamHI, EcoRI, EcoRV, HindIII, NotI, PstI, SacI, SpaI, XbaI and XhoI under conditions recommended by the manufacturer (Promega, Madison, Wis.). Approximately 3 µg of each digested sample was electrophoresed at 20 v for 18 hr through a 0.8% agarose gel in TAE buffer (0.04 M Trizma base, 0.02 M acetic acid, and 0.001 M EDTA, pH 8.3) containing 0.5 µg/ml ethidium bromide. Fragments were transferred to a Hybond N+ nylon filter (Amersham Pharmacia, Piscatatway, N.J.) using a VacuGene blotting apparatus (Amersham Pharmacia). To identify the 2-ketoreductase gene, the 400 bp fragment was obtained by digesting the pCR2.1™ plasmid with EcoRI, labeled using PCR DIG Probe Kit (Roche Biochemicals, Indianapolis, Ind.), and the labeled fragment was used as a probe.

Hybridization to the filter containing *G. oxydans* chromosomal digests, washing, and detection were performed according to materials and directions supplied with the DIG High Prime DNA Labeling and Detection Starter Kit II (Roche Biochemicals). Stringent wash conditions carried out using 1×SSC (20×SSC is 173.5 g NaCl, 88.2 g NaCl, pH 7.0) and 0.1% sodium dodecyl sulfate at 68° C. A single hybridizing fragment was visible in all the endonuclease digests. A 4 kb BamHI fragment was chosen for further analysis. Approximately 10 µg of *G. oxydans* chromosomal DNA was digested using 25 U BamHI for 2 hr at 37° C. in a final volume of 0.1 ml with the buffer recommended by the manufacturer (Promega). The digested DNA was electrophoresed on a 0.8% agarose gel in TAE buffer at 20 V for 18 hr. Fragments between 3.8 and 4.5 kb were identified by comparison to a 1 kb Plus DNA ladder (Invitrogen) and excised using a scalpel.

The DNA was isolated from the agarose using the QIAquick Gel Extraction Kit (QIAGEN) and ligated to BamHI-cleaved pZero2 (Invitrogen, Carlsbad, Calif.) vector DNA in a 2:1 molar ratio in a total volume of 10 µL at 22° C. for 2 hr. Two microliters of ligated DNA was used to transform 0.04 ml competent *E. coli* DH10B cells (Invitrogen) by electroporation. SOC medium was immediately added (0.96 ml; SOC is, per liter, 0.5% yeast extract, 2% tryptone, 10 mM NaCl, 2.5 mM KCl, 10 mM $MgCl_2$, 10 mM $MgSO_4$, and 20 mM glucose). Cells incubated in a shaker for 1 hr at 37° C. and 225 rpm.

Cells were spread onto a 132 mm Hybond N+ membrane placed on top of LB kanamycin agar medium. Kanamycin was purchased from Sigma Chemical Co., and used at final concentration of 50 µg/ml. Cells were grown at 37° C. for 20 hr. Colonies were replicated onto two fresh filters placed on top of LB kanamycin agar medium and incubated at 30° C. for 16 hrs. Colonies were lysed in situ by placing the filters on a piece of Whatman 3MM paper saturated with 0.5 M NaOH for 5 min. The filters were dried for 5 min on Whatman paper, then neutralized on 3MM paper soaked in 1.0 M Tris-HCl, pH 7.5 for 2 min, and dried again for 2 min. Membranes were placed on top of 3MM paper saturated with 1.0 M Tris-HCl, pH 7.0/1.5 M NaCl for 10 min.

DNA was crosslinked to the filters by exposure to ultraviolet light in a Stratagene UV Stratalinker 2400 set to "auto crosslink" mode (Stratagene, LaJolla, Calif.). Cell debris was removed from the membranes by immersing in 3×SSC/0.1% SDS, wiping the surface with a wetted Kimwipe®, then incubating in the same solution heated to 65° C. for 3 hr with agitation. Filters were rinsed with $dH_2O$ and used immediately or wrapped in SaranWrap® and stored at 4° C. Hybridization, washing, and detection was performed as described above using the 400 bp *G. oxydans* 2-ketoreductase gene probe.

Eight putative hybridizing colonies were picked from the master plate, inoculated into SOC medium containing kanamycin, and grown at 37° C. for 24 hr at 250 rpm. These colonies were also tested for the presence of 400 bp fragment with GOI1 and GOI4 primers using the conditions described previously. Six of the eight colonies gave the expected PCR 400 bp fragment confirming the BamHI fragment contained at least a portion of the 2-pentanone reductase gene. Cells from one milliliter of cell culture from two selected colonies were pelleted by centrifugation. Plasmid DNA was isolated using the QIAprep Spin Miniplasmid Isolation Kit (QIAGEN). An aliquot of plasmid DNA was digested with BamHI to confirm the presence of the 4.0 kb fragment.

Example 4

Sequencing and Sequence Analysis of G. oxydans 2 Ketoreductase-gene

DNA sequencing of the 4.0 kb insert of 2-ketoreductase gene was performed at the Bristol-Myers Squibb sequencing facility. DNA sequencing of the 4.0 kb insert was carried out using the BigDye terminator kit and DNA sequencing unit model 377 (Applied Biosystems, Foster City, Calif.). The complete 2-ketoreductase nucleotide sequence and predicted amino acid sequence is shown in FIGS. 1–1 to 1–3. The coding region was determined to be 780 bp in length. The nucleotide sequence was determined to encode a 260-amino acid protein (MW=27,220 daltons). The G. oxydans 2-ketoreductase amino acid sequence showed significant homology to other dehydrogenases including acetoin dehydrogenase, L-2,3-butanediol dehydrogenase, sorbitol dehydrogenase, polyketide reductase, and glucose dehydrogenase. In addition, the N-terminus of G. oxydans 2-ketoreductase showed homology to a ribitol-dehydrogenase from *Klebsiell aerogenes* (Loviny et. al., 1985, *Biochem. J.* 230:579–585).

A conserved domain search (CD-Search; http://www.ncbi.nlm.nih.gov/blast/Blast.cgi) indicated that *G. oxydans* 2-ketoreductase amino acid sequence included a short chain dehydrogenase domain (gnI|Pfam|pfam00106) extending though amino acid positions 4–255. In addition, BLAST 2.2.1 analysis (S. F. Altschul et al., 1997, *Nucleic Acids Res.* 25:3389–3402; http://www.ncbi.nlm.nih.gov/BLAST/) indicated that the amino acid sequence of the *G. oxydans* 2-ketoreductase shared 53% identity with the amino acid sequence of acetoin reductase and meso-2-,3-butanediol dehydrogenase from *Klebsiella pneumoniae* (GenBank Accession Nos. AAC78679 and BAA13085); 49% identity with the amino acid sequence of L-2,3-butanediol dehydrogenase from *Corynebacterium glutamicum* (GenBank Accession No. BAA36159); and 51% identity with the amino acid sequence of a putative short chain oxidoreductase from *Streptomyces coelicolor* (GenBank Accession No. T36396).

BLAST 2.2.1 analysis further indicated that longest stretch of identical contiguous amino acids shared by *G. oxydans* 2-ketoreductase and *K. pneumoniae* acetoin reductase was 9 residues in length. The longest stretch of identical contiguous amino acids shared by *G. oxydans* 2-ketoreductase and *K. pneumoniae* meso-2-,3-butanediol dehydrogenase was 8 residues in length. The longest stretch of identical contiguous amino acids shared by *G. oxydans* 2-ketoreductase and *C. glutamicum* L-2,3-butanediol dehydrogenase was 7 residues in length. The longest stretch of identical contiguous amino acids shared by *G. oxydans* 2-ketoreductase and *Streptomyces coelicoloroxidoreductase* was 11 residues in length.

The *G. oxydans* 2-ketoreductase nucleotide sequence did not show significant homology to previously identified enzymes. BLAST 2.2.1 analysis indicated that he longest stretch of identical contiguous nucleotides shared by *G. oxydans* 2-ketoreductase and other known nucleotide sequences was 20 bases in length.

Example 5

Subcloning and Expression of G. oxydans 2-Ketoreductase in E. coli

To facilitate PCR-based cloning of the 2 ketoreductase gene into expression vector pBMS2000 (disclosed in U.S. Pat. No. 6,068,991, issued May 30, 2000 to S. W. Liu et al.), oligonucleotide primers containing the 5' and 3' end of the gene along with compatible restriction endonuclease cleavage sites were prepared to include the following sequence:

5' ggaattccatatgtcctttctggaaaatcgc 3' (5' end of gene; SEQ ID NO:9)

NdeI

5' cggggatcctctcagcggaaaacg 3' (3' end of gene; antisense; SEQ ID NO:10)

BamHI

High-fidelity amplification of the 2-ketoreductase gene was carried out in four 25 µl aliquots, each consisting of 1× Z-Taq reaction buffer (PanVera Co., Madison, Wis.), 0.2 µM each deoxynucleotide triphosphate (dATP, dCTP, dGTP, dTTP), 0.4 nM each oligonucleotide, 2.5 U Z-Taq DNA polymerase (PanVera), and 10 pg plasmid DNA containing the cloned 2-ketoreductase gene. The amplification conditions included incubation at 94° C. for 4 min followed by 25 cycles of incubation at 94° C. for 1 min; 50° C. for 1 min; and 72° C. for 1.5 min using a Perkin-Elmer Model 480 thermocycler with autoextension. The PCR samples were electrophoresed on a 1.0% TAE agarose gel for 2 hr at 100 V. The 780 bp fragment containing the 2-ketoreductase gene was excised from the gel and purified using the QIAquick Gel Extraction Kit (QIAGEN).

The concentrations of the isolated DNAs were estimated by electrophoresis with the Low Molecular Weight DNA Mass Ladder (Invitrogen). Purified DNA was digested with 20 U NdeI for 2 hr at 37° C. in a total volume of 20 µl, diluted to 40 µl with water. This was followed by digestion with 20 U of BamHI at 30° C. for 2 hr. The expression vector pBMS2000 was digested with these endonucleases in parallel. The digested samples were electrophoresed on a 1.0% TAE agarose gel for 2 hr at 100 V. The 800 bp and 4516 bp fragments containing the ketoreductase gene and plasmid DNA, respectively, were excised from the gel and purified using the QIAquick Gel Extraction Kit (QIAGEN).

The concentrations of the isolated DNAs were estimated by electrophoresis and comparison with Low Molecular Weight DNA Mass Ladder (Invitrogen). Ligation and transformation were carried out as described above. Cells containing plasmid were selected on LB agar containing 20 µg/ml neomycin at 37° C. for 20 hr. Plasmids with the desired insert were screened by colony PCR as described earlier. Neomycin-resistant colonies were picked using a disposable plastic inoculation needle, swirled into LB broth, and then transferred to LB-neomycin agar. PCR samples were electrophoresed on a 0.8% TAE agarose gel for 2 hr at 100 V. Seven samples out of ten showed a strong band at 800 bp. One colony containing this plasmid (named pBMS2000-KR) was chosen for further study. The cloned *G. Oxydans* 2-ketoreductase gene was deposited at the American Type Culture Collection (ATCC), 10801 University Boulevard, Manassas, Va. 20110-2209 on Nov. 15, 2001 in *E. coli* cells as SC16469 under ATCC Accession No. PTA-3864 according to the terms of the Budapest Treaty.

The recombinant plasmid was transformed into *E. coli* strain BL21 (DE3) (Invitrogen, Carlsbad, Calif.) by electroporation. Transformed cells were selected on LB-neomycin agar medium, and individual colonies were inoculated into 10 ml MT3 medium (1.0% NZAmine A, 2.0% Yeastamin, 2.0% glycerol, 0.6% $Na_2HPO_4$, 0.3% $KH_2PO_4$, 0.125% $(NH_4)_2SO_4$, and 0.0246% $MgSO_4$) containing 30 μg/ml neomycin. The cultures were incubated at 28° C. at 250 rpm for 20 hr. Cultures were then diluted in fresh medium, grown to an $OD_{600}$ nm of 0.25, and then incubated under the same conditions until the $OD_{600}$ reached 0.8±0.1. IPTG was added to a final concentration of 0.3 mM and the cultures grown at the above conditions for 20 hr. Cells were pelleted by centrifugation (5,000×g) for 7 min. The culture medium was removed, and cells were washed with an equal volume ice cold 50 mM $KPO_4$ buffer (pH 7.3) with 2 mM dithiothreitol. The cells were again pelleted, and the wet cell weight was recorded.

Example 6

Reduction of 2-Pentanone Using Recombinant 2-Ketoreductase

To demonstrate the utility of the recombinant enzyme, the cloned ketoreductase was used in the reduction of 2-pentanone to 2-pentanol. The reaction contained 0.18 mg NAD+, 30 mg sodium formate, 0.3 units formate dehydrogenase (Sigma, St. Louis, Mo.), 2 mg 2-pentanone, and 0.5 ml of extract from an *E. coli* (BL21(DE3)) culture containing the pBMS2000-KR plasmid and expressing the ketoreductase. Alternatively, *P. pastoris* formate dehydrogenase (see S. Goldberg et al.: U.S. Provisional Patent Application Ser. No. 60/341,934 filed Dec. 19, 2001; U.S. Provisional Application Ser. No. 60/375,530 filed Apr. 25, 2002; and U.S. patent application Ser. No. 10/320,300; the contents of which are hereby incorporated by reference in their entirety) can be substituted for the commercial formate dehydrogenase. Cell extracts were obtained as follows: 2 g recombinant cells was suspended in 10 ml Buffer A (50 mM Tris-HCl, pH 7.5, 1 mM $CaCl_2$, and 1 mM $MgCl_2$). The resuspended cells were sonicated for 2 min (20 sec pulse "on" and 30 sec pulse "off") using Model 550 Sonic Dismembrator (Misonix Inc., Farmingdale, N.Y.). The resulting mixture was centrifuged for 15 min at 8000 rpm at 4° C. The supernatant was removed and used for reduction reactions. The reactions were carried out in a culture tube at 28° C. with shaking at 200 rpm. After 16 hr, samples were quenched with 2 ml of ethyl acetate and analyzed by gas chromatography (described earlier). There was complete reduction of the substrate using recombinant enzyme, while no reaction took place in the absence of recombinant enzyme.

Example 7

Reduction of Other Alkylketones Using Recombinant 2-Ketoreductase

To demonstrate the utility of the recombinant enzyme in the reduction of other substrates, the cloned ketoreductase was used in the reduction of 2-heptanone, 2-octanone, and 2-decanone. The reactions contained 0.18 mg NAD+, 30 mg sodium formate, 0.3 units formate dehydrogenase (purchased from Sigma), 2 mg 2-ketones, and 0.5 ml of extract from the *E. coli* culture containing the pBMS2000-KR plasmid and expressing the ketoreductase (described above). The reactions were carried out in a culture tube at 28° C. on a shaker at 200 rpm. The end of 16 hr, samples were quenched with 2 ml of ethyl acetate and analyzed by gas chromatography (described earlier). There was complete reduction of the substrates using recombinant enzyme as shown in the following table.

| Substrate | Product | % Conversion |
| --- | --- | --- |
| 2-Heptanone | 2-Heptanol | >98 |
| 2-Octanone | 2-Octanol | >98 |
| 2-Decanone | 2-Decanol | >98 |

No reaction took place in the absence recombinant enzyme.

The experiments described in Examples 1–7 are also described in S. Goldberg et al.: U.S. Provisional Patent Application Ser. No. 60/341,934 filed Dec. 19, 2001; U.S. Provisional Application Ser. No. 60/375,530 filed Apr. 25, 2002; and U.S. patent application Ser. No. 10/320,300; the contents of which are hereby incorporated by reference in their entirety.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which the present invention pertains.

What is claimed is:

1. An isolated polynucleotide comprising a nucleotide sequence encoding amino acid sequence SEQ ID-NO:2.

2. An isolated polynucleotide comprising a nucleotide sequence encoding the short chain dehydrogenase domain of amino acid sequence SEQ ID NO:2, wherein said polynucleotide encodes a polypeptide having 2-ketoreductase activity, and wherein the short chain dehydrogenase domain of amino acid sequence SEQ ID NO:2 is amino acids 4–255 of SEQ ID NO:2.

3. An isolated polynucleotide of claim 1 comprising: (a) the nucleotide sequence SEQ ID NO:1; (b) the coding region of (a); or (c) a nucleotide sequence that differs from (a) or (b) due to degeneracy of the genetic code.

4. An isolated polynucleotide comprising a nucleotide sequence which is complementary to a nucleotide sequence of claim 1.

5. An isolated polynucleotide which hybridizes under high stringency conditions to any one of: (a) the nucleotide sequence SEQ ID NO:1; (b) the coding region of (a); (c) the complement of (a); (d) the complement of (b); or (e) a nucleotide sequence that differs from (a), (b), (c) or (d) due to degeneracy of the genetic code; wherein said polynucleotide encodes a polypeptide having 2-ketoreductase activity, and wherein said high stringency conditions are hybridization in 50% formamide, 5×Denhardt's solution, 5×SSPE, and 0.2% SDS at 42° C., followed by washing in 0.1×SSPE and 0.1% SDS at 65° C.

6. A vector transferred or transfected with the isolated polynucleotide of claim 1.

7. A host cell comprising a vector of claim 6, wherein the host cell is selected from the group consisting of bacterial, fungal, insect, mammalian, and plant cells.

8. An isolated polynucleotide comprising the nucleotide sequence encoding a 2-ketoreductase contained in the plasmid in the ATCC deposit designated PTA-3864.

9. A method for producing a recombinant polypeptide comprising the amino acid sequence SEQ ID NO:2 comprising:

a) culturing a host cell of claim 7 under conditions suitable for the production of a recombinant polypeptide; and b) recovering the recombinant polypeptide comprising the amino acid sequence SEQ ID NO:2 from the host cell or host cell culture, thereby producing the recombinant polypeptide.

10. The isolated polynucleotide of claim 2, wherein said polypeptide shares at least 95% sequence identity with the amino acid sequence SEQ ID NO:2.

11. An isolated polynucleotide comprising a nucleotide sequence encoding a polypeptide that shares at least 95% sequence identity with amino acid sequence SEQ ID NO:2, wherein said polynucleotide encodes a polypeptide having 2-keroreductase activity.

12. A vector comprising the isolated polynucleotide of claim 5, 10 or 11.

* * * * *

UNITED STATES PATENT AND TRADEMARK OFFICE
CERTIFICATE OF CORRECTION

| | | |
|---|---|---|
| PATENT NO. | : 6,929,935 B2 | Page 1 of 1 |
| APPLICATION NO. | : 10/320104 | |
| DATED | : August 16, 2005 | |
| INVENTOR(S) | : Nanduri et al. | |

It is certified that error appears in the above-identified patent and that said Letters Patent is hereby corrected as shown below:

In Claim 6, Column 41, line 48, "transferred or transfected with" should read --comprising--.

In Claim 7, Column 42, line 20, "comprising" should read --transformed or transfected with--.

Signed and Sealed this

Eleventh Day of September, 2007

JON W. DUDAS
*Director of the United States Patent and Trademark Office*

SEQUENCE LISTING

<160> NUMBER OF SEQ ID NOS: 10

<210> SEQ ID NO 1
<211> LENGTH: 1575
<212> TYPE: DNA
<213> ORGANISM: Gluconobacter oxydans
<220> FEATURE:
<221> NAME/KEY: misc_feature
<222> LOCATION: (45)..(109)
<223> OTHER INFORMATION: wherein y = c or t

```
<220> FEATURE:
<221> NAME/KEY: misc_feature
<222> LOCATION: (40)..(1557)
<223> OTHER INFORMATION: wherein k = t or g
<220> FEATURE:
<221> NAME/KEY: misc_feature
<222> LOCATION: (51)..(186)
<223> OTHER INFORMATION: wherein r = a or g
<220> FEATURE:
<221> NAME/KEY: misc_feature
<222> LOCATION: (1381)..(1382)
<223> OTHER INFORMATION: wherein m = a or c
<220> FEATURE:
<221> NAME/KEY: misc_feature
<222> LOCATION: (20)..(21)
<223> OTHER INFORMATION: wherein v = a or c or g
<220> FEATURE:
<221> NAME/KEY: misc_feature
<222> LOCATION: (65)..(1346)
<223> OTHER INFORMATION: wherein b = c or t or g
<220> FEATURE:
<221> NAME/KEY: misc_feature
<222> LOCATION: (10)..(1294)
<223> OTHER INFORMATION: wherein s = c or g
<220> FEATURE:
<221> NAME/KEY: misc_feature
<222> LOCATION: (7)..(126)
<223> OTHER INFORMATION: wherein d = a or t or g
<220> FEATURE:
<221> NAME/KEY: misc_feature
<222> LOCATION: (6)..(1456)
<223> OTHER INFORMATION: wherein n = a or t or c or g

<400> SEQUENCE: 1
cggggnddds ggnsggcggv vataggcgnd gdaccscctk ddttycccgg raagaagaca      60
tsssbcycat ggatggaaat ttccccatga tgcccatgga tttcccssyt gaagatcatc    120
cggsgdaaac gaaggcatcg tnacgccctg gatttcggga atatgdacgg acgacaccag    180
gacctraagc cattccctca tcgctgatgc caccaaaggt ctcaaaaacg cactaatgc     240 tgtccgtgtg gttcatcaag tcctgccgag gctcttcgta acgtttattt aacgcatcct    300
cgcaggcccg gaaacagatg accagagtag gtttatgaaa attatcctta cccaggacag    360
gccccgtccc ctttgacaca atcctgtgtc aggcctgccg aacaggcgtt tttttgtgga    420
atacggaaag caaagggttg atggttcccg ccgtcatggc agtcacatgc cgatgacgga    480
caatcgaagg atctttttc aatgtccctt tctggaaaaa tcgccgcagt cacgggtgca     540
gcccagtgta tcggcaaggc cattgcgctt cgtctggcca aggatggcgc ggatgtcatc    600
ctgctcgacg tcaagcagga cacgcttgcc gaaaccgcaa aggaagttga agctctcggc    660
cggcgcgctg tggccctgac ggccgatatc agcaaccgcg accagttccg cagcacgctg    720
gccgatgcag caaagacgct cggcggcctg gacatcatgg tcaacaatgc ggggatctgt    780
caggtcaagc cgatcctgga catcgagcct gcggaaatcg agaagatctt cagcatcaac    840
gttcagggcg tgctctgggg catgcaggcg gctgcgaccc tcttcaagga aagggcacc     900 aagggcaaga tcatcaatgc ctgctcgatc gccggccatg aaggctatcc ccttctgggc    960
gcctattccg cgaccaaatt cgccgtccgc gccctgacgc agtcggccgc caaggaactc   1020
gcgtcctcgg gcattaccgt caattcctac tgccccggca ttgtcggaac cgacatgtgg   1080
gtcacgatcg acaagcgcat ggccgaaatc accggtacgg aaatcggcgc gacctacaag   1140
aaatacgttg aaggaatcgc tcttggccgc gtggagacgg cggacgatgt ggcgggcttc   1200
gtcgcctatt tgtccagcag tgacgccgat tacatgacgg gtcagtccgt cctgatcaac   1260
ggtggtcccg ttttccgctg agatcataaa aaasagggcc ggtttcccgc gccccctttt   1320
```

```
ttgtcagcgg ccgatcagac ggccgbgctg ccaggcttcg gcggcccctt ccgggtcctg    1380
mmcttcaacg gaaatgacat agtccagggc gctcatgacc ctgttgccaa gcatcatttc    1440
cgaaagctcg tcgagnagat cgctgtccgc ctgacgggcc acatcttcac gcatgatcat    1500
ccgggccgac atttctccgc ccagcaggtg ggccggatcg agctcggta ccaagcktga    1560 tgcatagctt gagta                                                    1575
```

<210> SEQ ID NO 2
<211> LENGTH: 259
<212> TYPE: PRT
<213> ORGANISM: Gluconobacter oxydans

<400> SEQUENCE: 2

```
Met Ser Leu Ser Gly Lys Ile Ala Ala Val Thr Gly Ala Ala Gln Cys
 1               5                  10                  15

Ile Gly Lys Ala Ile Ala Leu Arg Leu Ala Lys Asp Gly Ala Asp Val
            20                  25                  30

Ile Leu Leu Asp Val Lys Gln Asp Thr Leu Ala Glu Thr Ala Lys Glu
        35                  40                  45

Val Glu Ala Leu Gly Arg Arg Ala Val Ala Leu Thr Ala Asp Ile Ser
    50                  55                  60

Asn Arg Asp Gln Phe Arg Ser Thr Leu Ala Asp Ala Ala Lys Thr Leu
65                  70                  75                  80

Gly Gly Leu Asp Ile Met Val Asn Asn Ala Gly Ile Cys Gln Val Lys
                85                  90                  95

Pro Ile Leu Asp Ile Glu Pro Ala Glu Ile Glu Lys Ile Phe Ser Ile
            100                 105                 110

Asn Val Gln Gly Val Leu Trp Gly Met Gln Ala Ala Thr Leu Phe
        115                 120                 125

Lys Glu Lys Gly Thr Lys Gly Lys Ile Ile Asn Ala Cys Ser Ile Ala
    130                 135                 140

Gly His Glu Gly Tyr Pro Leu Leu Gly Ala Tyr Ser Ala Thr Lys Phe
145                 150                 155                 160

Ala Val Arg Ala Leu Thr Gln Ser Ala Ala Lys Glu Leu Ala Ser Ser
                165                 170                 175

Gly Ile Thr Val Asn Ser Tyr Cys Pro Gly Ile Val Gly Thr Asp Met
            180                 185                 190

Trp Val Thr Ile Asp Lys Arg Met Ala Glu Ile Thr Gly Thr Glu Ile
        195                 200                 205

Gly Ala Thr Tyr Lys Lys Tyr Val Glu Gly Ile Ala Leu Gly Arg Val
    210                 215                 220

Glu Thr Ala Asp Asp Val Ala Gly Phe Val Ala Tyr Leu Ser Ser Ser
225                 230                 235                 240

Asp Ala Asp Tyr Met Thr Gly Gln Ser Val Leu Ile Asn Gly Gly Pro
                245                 250                 255

Val Phe Arg
```

<210> SEQ ID NO 3
<211> LENGTH: 8
<212> TYPE: PRT
<213> ORGANISM: Bacteriophage T7

<400> SEQUENCE: 3

```
Asp Tyr Lys Asp Asp Asp Lys
 1               5
```

```
<210> SEQ ID NO 4
<211> LENGTH: 15
<212> TYPE: PRT
<213> ORGANISM: Gluconobacter oxydans

<400> SEQUENCE: 4

Ser Leu Ser Gly Lys Ile Ala Ala Val Thr Gly Ala Ala Gln Gly
1               5                   10                  15

<210> SEQ ID NO 5
<211> LENGTH: 11
<212> TYPE: PRT
<213> ORGANISM: Gluconobacter oxydans

<400> SEQUENCE: 5

Lys Arg Met Ala Glu Ile Thr Gly Thr Glu Ile
1               5                   10

<210> SEQ ID NO 6
<211> LENGTH: 10
<212> TYPE: PRT
<213> ORGANISM: Gluconobacter oxydans

<400> SEQUENCE: 6

Lys Val Glu Ala Leu Gly Arg Arg Ala Val
1               5                   10

<210> SEQ ID NO 7
<211> LENGTH: 29
<212> TYPE: DNA
<213> ORGANISM: Gluconobacter oxydans
<220> FEATURE:
<221> NAME/KEY: misc_feature
<222> LOCATION: (6)..(27)
<223> OTHER INFORMATION: wherein n = deoxyinosine (i)
<220> FEATURE:
<221> NAME/KEY: misc_feature
<222> LOCATION: (13)..(13)
<223> OTHER INFORMATION: wherein y = c or t
<220> FEATURE:
<221> NAME/KEY: misc_feature
<222> LOCATION: (3)..(9)
<223> OTHER INFORMATION: wherein r = a or g
<220> FEATURE:
<221> NAME/KEY: misc_feature
<222> LOCATION: (19)..(22)
<223> OTHER INFORMATION: wherein m = a or c

<400> SEQUENCE: 7
aargtngarg cytnggnmg nmgngcngt                                          29

<210> SEQ ID NO 8
<211> LENGTH: 26
<212> TYPE: DNA
<213> ORGANISM: Gluconobacter oxydans
<220> FEATURE:
<221> NAME/KEY: misc_feature
<222> LOCATION: (6)..(21)
<223> OTHER INFORMATION: wherein n = deoxyinosine (i)
<220> FEATURE:
<221> NAME/KEY: misc_feature
<222> LOCATION: (3)..(18)
<223> OTHER INFORMATION: wherein y = c or t

<400> SEQUENCE: 8
atytcngtnc cngtnatytc ngccat                                            26
```

```
<210> SEQ ID NO 9
<211> LENGTH: 32
<212> TYPE: DNA
<213> ORGANISM: Gluconobacter oxydans

<400> SEQUENCE: 9
ggaattccat atgtcccttt ctggaaaatc gc                                    32

<210> SEQ ID NO 10
<211> LENGTH: 23
<212> TYPE: DNA
<213> ORGANISM: Gluconobacter oxydans

<400> SEQUENCE: 10
cgggatcctc tcagcggaaa acg                                              23
```